United States Patent
Russo et al.

(10) Patent No.: US 11,078,163 B2
(45) Date of Patent: Aug. 3, 2021

(54) PROCESSES FOR THE SYNTHESIS OF SUBSTITUTED UREA COMPOUNDS

(71) Applicant: BIAL-PORTELA & Ca, S.A., S. Mamede do Coronado (PT)

(72) Inventors: Domenico Russo, S. Mamede do Coronado (PT); Jorge Bruno Reis Wahnon, S. Mamede do Coronado (PT); William Maton, S. Mamede do Coronado (PT); Tibor Eszenyi, Tiszalök (HU)

(73) Assignee: BIAL-PORTELA & Cª, S.A., S. Mamede do Coronado (PT)

( * ) Notice: Subject to any disclaimer, the term of this patent is extended or adjusted under 35 U.S.C. 154(b) by 0 days.

(21) Appl. No.: 16/512,872

(22) Filed: Jul. 16, 2019

(65) Prior Publication Data

US 2020/0140391 A1     May 7, 2020

Related U.S. Application Data

(63) Continuation of application No. 15/113,619, filed as application No. PCT/PT2015/000009 on Jan. 23, 2015, now abandoned.

(30) Foreign Application Priority Data

Jan. 24, 2014    (GB) ..................... 1401198

(51) Int. Cl.
     *C07D 233/64*      (2006.01)
     *C07D 401/04*      (2006.01)
     (Continued)

(52) U.S. Cl.
     CPC .......... *C07D 233/64* (2013.01); *C07C 209/68* (2013.01); *C07D 233/61* (2013.01); *C07D 401/04* (2013.01); *C07C 2601/08* (2017.05)

(58) Field of Classification Search
     CPC .................................................. C07D 233/64
     (Continued)

(56) References Cited

U.S. PATENT DOCUMENTS 1,316,280 A    9/1919   Curtiss
4,602,927 A    7/1986   Dockner et al.
(Continued)

FOREIGN PATENT DOCUMENTS

WO    2010074588 A2    7/2010
WO    2011050016 A1    4/2011
(Continued)

OTHER PUBLICATIONS

Anonymous: "Reaxys," XP055177239; Retrieved from the Internet: URL:https://www.reaxys.com/reaxys/secured/paging.do?performed=true&action=restore [retrieved on Mar. 17, 2015], pp. 1-3.
(Continued)

*Primary Examiner* — Joseph R Kosack
*Assistant Examiner* — Sagar Patel
(74) *Attorney, Agent, or Firm* — Banner & Witcoff, Ltd.

(57) ABSTRACT

The present invention concerns a process for preparing a compound having the Formula A; or a pharmaceutically acceptable salt or derivative thereof, or for preparing a substituted urea compound of Formula IIa, or a pharmaceutically acceptable salt or ester thereof, the process comprising the reaction of an imidazolyl intermediate of Formula IIa' with a carbamoyl halide of the formula: R1R2NC(=O)Hal, wherein Hal represents Cl, F, I or Br, wherein the intermediate of Formula IIa' is prepared by oxidation of the derivative of R5 and R6, R6-C(=O)CH$_2$R5 to form a glyoxal intermediate R6-C(=O)(C=O)R5, which is subjected to treatment with ammonium hydroxide and an aldehyde R8CHO to provide the intermediate of Formula IIa' and wherein the compound substituents are as defined herein.

12 Claims, No Drawings

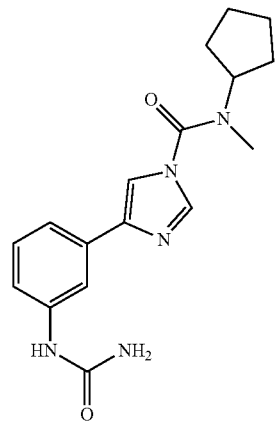

Formula A

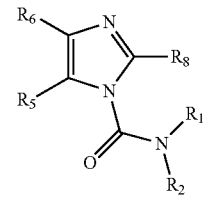

Formula IIa

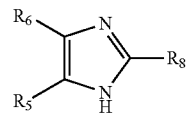

Formula IIa'

(51) Int. Cl.
*C07D 233/61* (2006.01)
*C07C 209/68* (2006.01)

(58) Field of Classification Search
USPC .......... 548/334.1, 343.5, 341.5, 342.5, 338.1
See application file for complete search history.

(56) References Cited

U.S. PATENT DOCUMENTS

| | | | |
|---|---|---|---|
| 4,643,999 | A | 2/1987 | Tully |
| 4,859,691 | A | 8/1989 | Bowman |
| 5,852,192 | A * | 12/1998 | Himmelsbach ...... C07D 211/58 546/210 |
| 9,549,915 | B2 * | 1/2017 | Rosa .......................... A61P 3/00 |
| 10,023,541 | B2 * | 7/2018 | Rosa ........................ A61P 25/16 |
| 2010/0036121 | A1 | 2/2010 | Turchetta et al. |
| 2015/0174103 | A1 | 6/2015 | Rosa et al. |
| 2015/0197503 | A1 | 7/2015 | Russo et al. |
| 2017/0101381 | A1 | 4/2017 | Rosa et al. |
| 2019/0135764 | A1 * | 5/2019 | Rosa .......................... A61P 3/00 |

FOREIGN PATENT DOCUMENTS

| | | | |
|---|---|---|---|
| WO | 2014017936 | A2 | 1/2014 |
| WO | WO-2014017936 | A2 * | 1/2014 ................ A61P 9/12 |

OTHER PUBLICATIONS

Bahrami et al., "One-pot synthesis of 1,2,4,5-tetrasubstituted and 2,4,5-trisubstituted imidazoles by zinc oxide as efficient and reusable catalyst," Monatshefte Für Chemie—Chemical Monthly, Dec. 16, 2010, vol. 142, No. 2, pp. 159-162.
Cao et al., J. Chem. Res. 2011, 35, 600-601.
International Search Report for Serial No. PCT/PT2015/000009, dated Jul. 28, 2015, 6 pages.
Ishida et al., "Molecular Conformations of Aminophenylimidazoles Exhibiting Antiulcer Activities," Chem. Pharm. Bull. 38, 1803-09, 1990.
Koga et al., Bioorg. Med. Chem. Lett. 8, 1471, 1998.
Zheng et al., "Asymmetric Carbonyl-Ene Reaction Catalyzed by Chiral N,N?-Dioxide-Nickel(II) Complex: Remarkably Broad Substrate Scope," J. Am. Chem. Soc. 130, 15770-71, 2008.

* cited by examiner

PROCESSES FOR THE SYNTHESIS OF SUBSTITUTED UREA COMPOUNDS

The present invention relates to processes for the synthesis of substituted urea compounds and for intermediates useful in the production of such compounds. In particular, though not exclusively, it relates to processes for synthesising certain active pharmaceutical ingredients having a heteroaryl N-carboxamide core.

Molecules containing urea functional groups are of interest in medicinal chemistry. A common method for their preparation is to convert a first amine component to an isocyanate or activated carbamate, followed by reaction with a second amine component. However, this approach is not available when neither of the amine components is a primary amine. In particular, secondary amines cannot be converted to isocyanates, and secondary carbamates are known to suffer from low reactivity in the required nucleophilic substitution reaction with the second amine component (see Lee et al. (2004) *Tetrahedron* 60, 3439). Complex or harsh approaches have thus been used in these circumstances, e.g. the aluminium amide approach described by Lee et al. (above).

A number of molecules having fatty acid amide hydrolase (FAAH) inhibitory activity and containing urea groups are disclosed in WO 2010/074588. For example, a subgroup of the compounds disclosed in this document contain an imidazole-1-carboxamide motif. These compounds are generally prepared using an approach comprising carbamoylation of 1H-imidazole derivatives with carbamoyl chlorides. For illustrative purposes, 3-(1-(cyclohexyl(methyl)carbamoyl)-1H-imidazol-4-yl)pyridine-1-oxide is prepared by reaction of the imidazolylpyridine hydrochloride with potassium 2-methylpropan-2-olate in a mixed solvent of tetrahydrofuran (THF) and dimethylformamide (DMF), followed by addition of a catalytic amount of pyridine and N,N-dimethylpyridine-4-amine, this step being followed by addition of cyclohexyl(methyl)carbamic chloride. This mixture is kept at elevated temperature overnight, following which a non-oxidised intermediate can be extracted in low yield.

This intermediate is then oxidised to give the final compound. A similar approach to urea formation using cyclohexyl(methyl)carbamic chloride is described in Koga et al. (1998) *Bioorg. Med. Chem. Lett.* 8, 1471. The solvent used for urea formation in this instance is DMF.

The main limitation of the above procedure disclosed in WO 2010/074588 is the very low overall yield. This problem is addressed in WO 2012/015324, wherein the ureas of WO 2010/074588 are synthesised using an alternative approach based on the reaction of a phenylcarbamate derivative of an N-containing heteroaryl group with a primary or secondary amine. The yield using the phenylcarbamate approach is reported to be much improved, and WO 2012/015324 discourages the use of the carbamoyl chloride approach.

For the preparation of 1H-imidazole derivatives, previous methods have involved the preparation of α-amino ketones as the key precursor in the ring formation reaction to produce the imidazole structure. The synthesis of the α-amino ketones can be achieved, for example, by employing routes via α-halo ketones (Sorrell et al., *J. Org. Chem.*, 1994, 59, 1589; WO 2006/047167) and/or α-azido ketones (Prakash et al., *Molecules*, 2006, 11, 523), or oxime sulfonates (Clemo et al. *J. Chem. Soc.*, 1938, 753). However, such routes are complex multistep procedures employing particularly hazardous reagents.

A process for the production of substituted imidazoles is also described by Cao et al. (*J. Chem. Res.*, 2011, 35, 600). However, the process has proved to be limited in its utility to a restricted range of structural motifs, particularly by the extraction steps of the process.

Therefore, there exists a need to provide an efficient approach for the formation of substituted ureas and precursors thereof, particularly (but not exclusively) those containing an imidazole-1-carboxamide core.

According to a first aspect of the present invention, there is provided a process for preparing a compound having the Formula A:

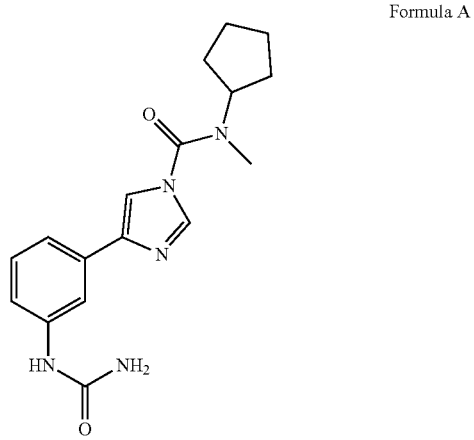 [SMILES: CN(C(=O)n1cnc(-c2cccc(NC(N)=O)c2)c1)C1CCCC1]

Formula A or a pharmaceutically acceptable salt or derivative thereof, or for preparing a substituted urea compound of Formula IIa, or a pharmaceutically acceptable salt or ester thereof,

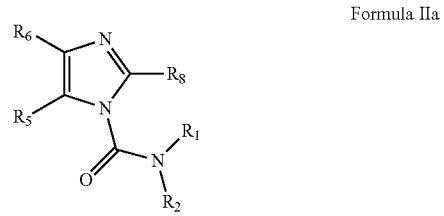

Formula IIa the process comprising the reaction of an imidazolyl intermediate of IIa',

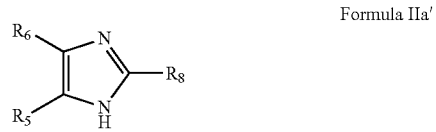

Formula IIa' with a carbamoyl halide of the formula: R1R2NC(=O)Hal, wherein Hal represents Cl, F, I or Br, wherein the intermediate of Formula IIa' is prepared by oxidation of the derivative of R5 and R6, R6-C(=O)CH₂R5 to form a glyoxal intermediate R6-C(=O)(C=O)R5, which is subjected to treatment with ammonium hydroxide and an aldehyde R8CHO to provide the intermediate of Formula IIa', wherein, in the case of preparation of the compound of Formula A, R6 is NH$_2$CONH-phenyl, or a nitrophenyl, aminophenyl or amino-protected aminophenyl precursor of this moiety which can be subjected to conversion to the NH$_2$CONH-phenyl group after urea formation, and R5 is H, R1 is methyl and R2 is cyclopentyl;

and wherein, in the case of preparation of a compound of Formula IIa, R1 and R2 can each be independently selected from H, C$_{1-20}$ alkyl, C$_{1-6}$ alkoxy, aryl, heteroaryl, partially or fully saturated heterocyclyl, C$_{3-10}$ cycloalkyl, aryl C$_{1-6}$ alkyl, heteroaryl C$_{1-6}$ alkyl, heterocyclyl C$_{1-6}$ alkyl, C$_{3-10}$ cycloalkyl C$_{1-6}$ alkyl, R1a, halogen, OH, OR1a, OCOR1a, SH, SR1a, SCOR1a, NH$_2$, NHR1a, NHSO$_2$NH$_2$, NHSO$_2$R1a, NR1aCOR1b, NHCOR1a, NR1aR1b, COR1a, CSR1a, CN, COOH, COOR1a, CONH$_2$, CONHOH, CONHR1a, CONHOR1a, SO$_2$R1a, SO$_3$H, SO$_2$NH$_2$, CONR1aR1b, SO$_2$NR1aR1b, wherein R1a and R1b are independently selected from C$_{1-6}$ alkyl, substituted C$_{1-6}$ alkyl, aryl, heteroaryl, C$_{3-8}$ cycloalkyl and heterocyclyl, or R1a and R1b, together with the heteroatom to which they are joined, can form heterocyclyl, wherein, when R1 or R2 is C$_{1-20}$ alkyl, alkoxy, aryl, heteroaryl, heterocyclyl, C$_{3-10}$ cycloalkyl, aryl C$_{1-6}$ alkyl, heteroaryl C$_{1-6}$ alkyl, heterocyclyl C$_{1-6}$ alkyl, C$_{3-10}$ cycloalkyl C$_{1-6}$ alkyl, or is a group containing one or more of these moieties, each of these moieties may optionally be substituted with one or more groups selected from R1c, halogen, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-10}$ alkyl, OH, OR1c, OCOR1c, SH, SR1c, SCOR1c, NH$_2$, NO$_2$, NHR1c, NHSO$_2$NH$_2$, NHSO$_2$R1c, NR1COR1d, NHC(NH)NH$_2$, NHCOR1c, NR1cR1d, COR1c, CSR1c, CN, COOH, COOR1c, CONH$_2$, CONHOH, CONHR1c, CONHOR1c, C(NOH)NH$_2$, CONR1cR1d, SO$_2$R1c, SO$_3$H, SO$_2$NH$_2$, SO$_2$NR1cR1d, wherein R1c and R1d are independently selected from C$_{1-6}$ alkyl, substituted C$_{1-6}$ alkyl, aryl, heteroaryl, C$_{3-8}$ cycloalkyl and heterocyclyl, or R1c and R1d, together with the heteroatom to which they are joined, can form heterocyclyl, wherein, when the substituent of R1 or R2 is C$_{1-10}$ alkyl, aryl, heteroaryl, heterocyclyl, C$_{1-6}$ alkoxy, aryloxy, heteroaryloxy, heterocyclyloxy, aryl C$_{1-6}$ alkyl, heteroaryl C$_{1-6}$ alkyl, heterocyclyl C$_{1-6}$ alkyl, aryl C$_{1-6}$ alkoxy, heteroaryl C$_{1-6}$ alkoxy, heterocyclyl C$_{1-6}$ alkoxy, C$_{1-6}$ alkylamino, C$_{1-6}$ dialkylamino, C$_{1-6}$ alkyl, C$_{3-8}$ cycloalkyl or is a group containing one or more of these moieties, each of these moieties may optionally be substituted with one or more groups selected from R1e, halogen, C$_{1-10}$ alkyl, OH, OR1e, OCOR1e, SH, SR1e, SCOR1e, NH$_2$, NO$_2$, NHR1e, NHSO$_2$NH$_2$, NHSO$_2$R1e, NR1eCOR1f, NHC(NH)NH$_2$, NHCOR1e, NR1eR1f, COR1e, CSR1e, CN, COOH, COOR1e, CONH$_2$, CONHOH, CONHOR1e, CONHR1e, C(NOH))NH$_2$, CONR1eR1f, SO$_2$R1e, SO$_3$H, SO$_2$NH$_2$, SO$_2$NR1eR1f, wherein R1e and R1f are independently selected from C$_{1-6}$ alkyl, substituted C$_{1-6}$ alkyl, aryl, heteroaryl, C$_{3-8}$ cycloalkyl and heterocyclyl, or R1e and R1f, together with the heteroatom to which they are joined, can form heterocyclyl, with the exception that R1 and R2 are not both H; or R1 and R2, together with the N to which they are attached, can form a heteroaryl or heterocyclyl group, each of which may optionally be substituted with one or more oxygen atoms or one or more groups selected from aryl, heteroaryl, partially or fully saturated heterocyclyl, C$_{3-8}$ cycloalkyl, C$_{1-6}$ alkyl, aryl C$_{1-6}$ alkyl, heteroaryl C$_{1-6}$ alkyl, heterocyclyl C$_{1-6}$ alkyl, C$_{3-8}$ cycloalkyl C$_{1-6}$ alkyl, C$_{1-6}$ alkoxy, aryloxy, heteroaryloxy, heterocyclyloxy, R2a, halogen, OH, OR2a, OCOR2a, SH, SR2a, SCOR2a, NH$_2$, NO$_2$, NHR2a, NHSO$_2$NH$_2$, NHSO$_2$R2a, NR2aCOR2b, NHC(NH)NH$_2$, NHCOR2a, NR2aR2b, COR2a, CSR2a, CN, COOH, COOR2a, CONH$_2$, CONHOH, CONHR2a, CONHOR2a, C(NOH)NH$_2$, CONR2aR2b, SO$_2$R2a, SO$_3$H, SO$_2$NH$_2$, SO$_2$NR2aR2b, wherein R2a and R2b are independently selected from C$_{1-6}$ alkyl, substituted C$_{1-6}$ alkyl, aryl, heteroaryl, C$_{3-8}$ cycloalkyl and heterocyclyl, or R2a and R2b, together with the heteroatom to which they are joined, can form heterocyclyl, wherein, when the substituent of the heteroaryl or heterocyclyl formed by R1 and R2 together is aryl, heteroaryl, heterocyclyl, C$_{3-8}$ cycloalkyl, C$_{1-6}$ alkyl, aryl C$_{1-6}$ alkyl, heteroaryl C$_{1-6}$ alkyl, heterocyclyl C$_{1-6}$ alkyl, C$_{3-8}$ cycloalkyl C$_{1-6}$ alkyl, C$_{1-6}$ alkoxy, aryloxy, heteroaryloxy, heterocyclyloxy, or a group containing one or more of these moieties, each of these moieties may optionally be substituted with one or more groups selected from halogen, hydroxyl, C$_{1-6}$ alkyl, aryl, heteroaryl, heterocyclyl, C$_{3-8}$ cycloalkyl, C$_{1-4}$ alkoxy, aryloxy, heteroaryloxy, heterocyclyloxy, C$_{3-8}$ cycloalkyloxy, aryl C$_{1-4}$ alkoxy, heteroaryl C$_{1-6}$ alkoxy, heterocyclyl C$_{1-4}$ alkoxy, C$_{3-8}$ cycloalkyl C$_{1-4}$ alkoxy, R2c, OR2e, OCOR2c, SH, SR2c, SCOR2c, NH$_2$, NO$_2$, NHR2c, NHSO$_2$NH$_2$, NHSO$_2$R2c, NR2cCOR2d, NHC(NH)NH$_2$, NHCOR2c, NR2cR2d, COR2c, CSR2c, CN, COOH, COOR2e, CONH$_2$, CONHOH, CONHR2c, CONHOR2c, C(NOH)NH$_2$, CONR2cR2d, SO$_2$R2c, SO$_3$H, SO$_2$NH$_2$, SO$_2$NR2cR2d, wherein R2c and R2d are independently selected from C$_{1-6}$ alkyl, substituted C$_{1-6}$ alkyl, aryl, heteroaryl, C$_{3-8}$ cycloalkyl and heterocyclyl, or R2c and R2d, together with the heteroatom to which they are joined, can form heterocyclyl, wherein, when the substituent of the substituent of the heteroaryl or heterocyclyl formed by R1 and R2 together is C$_{1-6}$ alkyl, aryl, heteroaryl, heterocyclyl, C$_{3-8}$ cycloalkyl, C$_{1-6}$ alkoxy, aryloxy, heteroaryloxy, heterocyclyloxy, C$_{3-8}$ cycloalkyloxy, aryl C$_{1-4}$ alkoxy, heteroaryl C$_{1-4}$ alkoxy, heterocyclyl C$_{1-4}$ alkoxy, C$_{3-8}$ cycloalkyl C$_{1-4}$ alkoxy, or is a group containing one or more of these moieties, each of these moieties may optionally be substituted with one or more groups selected from C$_{1-4}$ alkoxy, R2e, halogen, OH, OR2e, OCOR2e, SH, SR2e, SCOR2e, NH$_2$, NO$_2$, NHR2e, NHSO$_2$NH$_2$, NHSO$_2$R2e, NR2eCOR2f, NHC(NH)NH$_2$, NR2eR2f, NHCOR2e, COR2e, CSR2e, CN, COOH, COOR2e, CONH$_2$, CONHOH, CONHR2e, CONHOR2e, C(NOH)NH$_2$, CONR2eR2f, SO$_2$R2e, SO$_3$H, SO$_2$NH$_2$, SO$_2$NR2eR2f, wherein R2e and R2f are independently selected from C$_{1-6}$ alkyl, substituted C$_{1-6}$ alkyl, aryl, heteroaryl, C$_{3-8}$ cycloalkyl and heterocyclyl, or R2e and R2f, together with the heteroatom to which they are joined, can form heterocyclyl;

R5 together with the C to which it is attached, can form a carbonyl group with the double bonds in Formula Ida rearranged accordingly, or R5 is selected from H, C$_{1-6}$ alkyl, aryl, heteroaryl, heterocyclyl, C$_{3-8}$ cycloalkyl, C$_{1-6}$ alkoxy, aryloxy, heteroaryloxy, heterocyclyloxy, R5a, halogen, OH, OR5a, SH, SR5a, OCOR5a, SCOR5a, NH$_2$, NO$_2$, NHR5a, NHSO$_2$NH$_2$, NHSO$_2$R5a, NR5aCOR5b, NHCOR5a, NHC(NH)NH$_2$, NR5aR5b, COR5a, CSR5a, CN, COOH, COOR5a, CONH$_2$, CONHOH, CONHR5a, CONHOR5a, C(NOH)NH$_2$, CONR5aR5b, SO$_2$R5a, SO$_3$H, SO$_2$NH$_2$, SO$_2$NR5aR5b, wherein R5a and R5b are independently selected from C$_{1-6}$ alkyl, substituted C$_{1-6}$ alkyl, aryl, heteroaryl, $C_{3-8}$ cycloalkyl and heterocyclyl, or R5a and R5b, together with the heteroatom to which they are joined, can form heterocyclyl, wherein, when R5 is $C_{1-6}$ alkyl, aryl, heteroaryl, heterocyclyl, $C_{1-6}$ alkoxy, aryloxy, heteroaryloxy, heterocyclyloxy, $C_{1-6}$ alkyl, $C_{3-8}$ cycloalkyl, or is a group containing one or more of these moieties, each of these moieties may optionally be substituted with one or more groups selected from halogen, aryl, heteroaryl, heterocyclyl, $C_{1-6}$ alkoxy, aryloxy, heteroaryloxy, heterocyclyloxy, R5c, $C_{1-6}$ alkyl, OH, OR5c, OCOR5c, SH, SR5c, SCOR5c, $NH_2$, $NO_2$, NHR5c, $NHSO_2NH_2$, $NHSO_2R5c$, NR5cCOR5d, NHCOR5e, NHC(NH)$NH_2$, NR5cR5d, COR5c, CSR5c, CN, COOH, COOR5c, $CONH_2$, CONHOH, CONHR5c, CONHOR5c, C(NOH)$NH_2$, CONR5cR5d, $SO_2R5c$, $SO_3H$, $SO_2NH_2$, $SO_2NR5cR5d$, wherein R5c and R5d are independently selected from $C_{1-6}$ alkyl, substituted $C_{1-6}$ alkyl, aryl, heteroaryl, $C_{3-8}$ cycloalkyl and heterocyclyl, or R5c and R5d, together with the heteroatom to which they are joined, can form heterocyclyl, wherein, when the substituent of R5 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R5e, $C_{1-6}$ alkyl, OH, OR5e, OCOR5e, SH, SR5e, SCOR5e, $NH_2$, $NO_2$, NHR5e, $NHSO_2NH_2$, $NHSO_2R5e$, NR5eCOR5f, NHCOR5e, NHC(NH)$NH_2$, NR5eR5f, COR5e, CSR5e, CN, COOH, COOR5e, $CONH_2$, CONHOH, CONHR5e, CONHOR5e, C(NOH)$NH_2$, CONR5eR5f, $SO_2R5e$, $SO_3H$, $SO_2NH_2$, $SO_2NR5eR5f$, wherein R5e and R5f are independently selected from $C_{1-6}$ alkyl, substituted $C_{1-6}$ alkyl, aryl, heteroaryl, $C_{3-8}$ cycloalkyl and heterocyclyl, or R5e and R5f, together with the heteroatom to which they are joined, can form heterocyclyl;

R6 is selected from $C_{1-6}$ alkyl, aryl, heteroaryl, heterocyclyl, $C_{1-6}$ alkoxy, aryloxy, heteroaryloxy, heterocyclyloxy, R6a, halogen, OH, OR6a, SH, SR6a, OCOR6a, SCOR6a, $NH_2$, $NO_2$, NHR6a, $NHSO_2NH_2$, $NHSO_2R6a$, NR6aCOR6b, NHCOR6a, NHC(NH)$NH_2$, NR6aR6b, COR6a, CSR6a, CN, COOH, COOR6a, $CONH_2$, CONHOH, CONHR6a, CONHOR6a, C(NOH)$NH_2$, CONR6aR6b, $SO_2R6a$, $SO_3H$, $SO_2NH_2$, $SO_2NR6aR6b$, wherein R6a and R6b are independently selected from $C_{1-6}$ alkyl, substituted $C_{1-6}$ alkyl, aryl, heteroaryl, $C_{3-8}$ cycloalkyl and heterocyclyl, or R6a and R6b, together with the heteroatom to which they are joined, can form heterocyclyl, wherein, when R6 is heteroaryl or heterocyclyl, each of these moieties may optionally be substituted with one or more oxygen atoms, and when R6 is $C_{1-6}$ alkyl, aryl, heteroaryl, heterocyclyl, $C_{1-6}$ alkoxy, aryloxy, heteroaryloxy, heterocyclyloxy, $C_{3-8}$ cycloalkyl, or is a group containing one or more of these moieties, each of these moieties may optionally be substituted with one or more groups selected from halogen, R6c, $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, OH, OR6c, OCOR6c, SH, SR6e, SCOR6c, $NH_2$, $NO_2$, NHR6c, $NHSO_2NH_2$, NHC(NH)$NH_2$, $NHSO_2R6c$, NR6cCOR6d, NHCOR6c, NR6cR6d, COR6e, CSR6c, CN, COOH, COOR6c, $CONH_2$, CONHR6c, CONHOc, CONHOH, C(NOH)$NH_2$, CONR6cR6d, $SO_2R6c$, $SO_3H$, $SO_2NH_2$, $SO_2NR6cR6d$, wherein R6c and R6d are independently selected from $C_{1-6}$ alkyl, substituted $C_{1-6}$ alkyl, aryl, heteroaryl, $C_{3-8}$ cycloalkyl and heterocyclyl, or R6c and R6d, together with the heteroatom to which they are joined, can form heterocyclyl, wherein, when the substituent of R6 is heteroaryl or heterocyclyl, each of these moieties may optionally be substituted with one or more oxygen atoms, or when the substituent of R6 is $C_{1-6}$ alkyl, $C_{1-6}$ alkynyl, aryl, heteroaryl, heterocyclyl, $C_{1-6}$ alkoxy, aryloxy, heteroaryloxy, heterocyclyloxy, aryl $C_{1-6}$ alkyl, heteroaryl $C_{1-6}$ alkyl, heterocyclyl $C_{1-6}$ alkyl, aryl $C_{1-6}$ alkoxy, heteroaryl $C_{1-6}$ alkoxy, heterocyclyl $C_{1-6}$ alkoxy, $C_{3-8}$ cycloalkyl, or is a group containing one or more of these moieties, each of these moieties may optionally be substituted with one or more groups selected from halogen, R6e, $C_{1-6}$ alkyl, $C_{1-4}$ alkoxy, OH, OR6e, OCOR6e, SH, SR6e, SCOR6e, $NH_2$, $NO_2$, NHR6e, $NHSO_2NH_2$, NHC(NH)$NH_2$, $NHSO_2R6e$, NR6eCOR6f, NHCOR6e, NR6eR6f, COR6e, CSR6e, CN, COOH, COOR6e, $CONH_2$, CONHOH, CONHR6e, CONHOR6e, C(NOH)$NH_2$, CONR6eR6f, $SO_2R6e$, $SO_3H$, $SO_2NH_2$, $SO_2NR6eR6f$, wherein R6e and R6f are independently selected from $C_{1-6}$ alkyl, substituted $C_{1-6}$ alkyl, aryl, heteroaryl, $C_{3-8}$ cycloalkyl and heterocyclyl, or R6e and R6f, together with the heteroatom to which they are joined, can form heterocyclyl; and R8 is hydrogen or a group selected from $C_{1-6}$ alkyl, aryl, heteroaryl, heterocyclyl, and $C_{3-8}$ cycloalkyl, wherein each of these moieties may be optionally substituted with one or more groups selected from halogen, hydroxy, $C_{1-6}$ alkyl, $C_{1-6}$ haloalkyl, $C_{1-6}$ alkoxy, aryl, heteroaryl, heterocyclyl, aryloxy, heteroaryloxy, heterocyclyloxy, and acyl, wherein when the substituent of R8 is $C_{1-6}$ alkyl, $C_{1-6}$ alkoxy, or acyl, each of these moieties may optionally be substituted with one or more groups selected from halogen, hydroxy, $C_{1-6}$ alkoxy, heterocyclyl optionally substituted with 1 to 3 groups selected from halogen, $C_{1-6}$ alkyl, $C_{1-6}$ haloalkyl, and heteroaryl, $C_{1-6}$ alkylamino, and $C_{1-6}$ dialkylamino, and wherein when the substituent of R8 is aryl, heteroaryl, heterocyclyl, aryloxy, heteroaryloxy, or heterocyclyloxy, each of these moieties may optionally be substituted with one or more groups selected from halogen, hydroxy, $C_{1-6}$ alkoxy, $C_{1-6}$ alkylamino, $C_{1-6}$ dialkylamino, aryl optionally substituted with 1 to 3 groups selected from halogen and $C_{1-6}$ haloalkyl, and acyl.

Compared to other processes for producing the imidazole intermediates of Formula IIa', and for producing the ureas of Formula IIa, the process of the present invention provides a surprisingly beneficial approach to the production of such ureas and imidazoles. The route is more direct than certain other processes, and produces a satisfactory yield. A similar process for the production of substituted imidazoles is described by Cao et al. (*J. Chem. Res.*, 2011, 35, 600, see above). However, it was found that, for the compounds to be prepared according to the process of the invention, the method of Cao was not efficient.

In particular embodiments of this aspect, the carbamoyl halide is a carbamoyl chloride. The preparation of the carbamoyl chloride may be accomplished, for example, using a phosgene reagent. In embodiments, the oxidation of the derivative of R5 and R6 may employ an inorganic acid, such as HX, where X is a halogen atom. For example, HCl or HBr. HBr may be preferred. As solvent and oxidising reagent for this step, DMSO may be used.

As mentioned above, the processes of the present invention are useful for preparing compounds having FAAH inhibitory activity and containing urea groups, and in particular those compounds disclosed in WO 2010/074588. The compounds of WO 2010/074588 may be used in a variety of diseases or conditions in which the endogenous endocannabinoid system is implicated.

The term '$C_{x-y}$ alkyl' as used herein refers to a linear or branched saturated hydrocarbon group containing from x to y carbon atoms. For example, $C_{1-6}$ alkyl refers to a linear or branched saturated hydrocarbon group containing from 1 to 6 carbon atoms. Examples of $C_{1-6}$ alkyl groups include methyl, ethyl, n-propyl, isopropyl, n-butyl, isobutyl, sec-butyl, tert butyl, n-pentyl, isopentyl, neopentyl and hexyl. Preferably, the hydrocarbon group is linear. The groups $C_{1-20}$ alkyl and $C_{1-10}$ alkyl are preferably $C_{1-6}$ alkyl. The term '$C_{x-y}$ alkyl' is also used to mean a linear or branched saturated hydrocarbon group containing from x to y carbon atoms and in which a terminal methyl group is further substituted, i.e. so as to render a $C_{x-y}$ alkylene group.

The term '$C_{x-y}$ haloalkyl' as used herein refers to a $C_{1-6}$ alkyl group as defined herein wherein at least one hydrogen atom is replaced with halogen. Examples of such groups include fluoroethyl, trifluoromethyl and trifluoroethyl.

The term '$C_{x-y}$ alkynyl' as used herein refers to a linear or branched hydrocarbon group containing from x to y carbon atoms and at least one carbon-carbon triple bond. For example, $C_{1-6}$ alkynyl refers to a linear or branched hydrocarbon group containing from 1 to 6 carbon atoms. Examples of $C_{1-6}$ alkynyl groups include, ethynyl, methylbutynyl (e.g. 3-methyl-1-butynyl), 1,3-butadiynyl and 1,3,5-hexatriynyl.

The term 'aryl' as used herein refers to a $C_{6-12}$ monocyclic or bicyclic hydrocarbon ring wherein at least one ring is aromatic. Examples of such groups include phenyl, naphthalenyl and tetrahydronaphthalenyl.

The term 'heteroaryl' as used herein refers to a 5-6 membered monocyclic aromatic or a fused 8-10 membered bicyclic aromatic ring which monocyclic or bicyclic ring contains 1 to 4 heteroatoms selected from oxygen, nitrogen and sulphur. Examples of such monocyclic aromatic rings include thienyl, furyl, furazanyl, pyrrolyl, triazolyl, tetrazolyl, imidazolyl, oxazolyl, thiazolyl, oxadiazolyl, isothiazolyl, isoxazolyl, thiadiazolyl, pyranyl, pyrazolyl, pyrimidyl, pyridazinyl, pyrazinyl, pyridyl, triazinyl, tetrazinyl and the like. Examples of such bicyclic aromatic rings include quinolinyl, isoquinolinyl, quinazolinyl, quinoxalinyl, pteridinyl, cinnolinyl, phthalazinyl, naphthyridinyl, indolyl, isoindolyl, azaindolyl, indolizinyl, indazolyl, purinyl, pyrrolopyridyl, furopyridyl, benzofuranyl, isobenzofuranyl, benzothienyl, benzoimidazolyl, benzoxazolyl, benzoisoxazolyl, benzothiazolyl, benzoisothiazolyl, benzoxadiazolyl, benzothiadiazolyl and imidazopyridyl.

The term 'heteroaryl substituted with one or more oxygen atoms' refers to a heteroaryl ring which has one or more oxygen atoms bonded to the ring. It does not mean that the heteroaryl ring contains one or more oxygen atoms as ring atoms, although in some embodiments, this may be the case. Preferably, the one or more oxygen atoms is bonded to a nitrogen heteroatom in the heteroaryl ring. A heteroaryl substituted with an oxygen atom may contain an N-oxide. An example of a heteroaryl substituted with one or more oxygen atoms is 1-oxidopyridyl in which the pyridyl nitrogen is oxidised.

The term 'heterocyclyl' refers to a 3-8 (preferably 4-8 and, more preferably, 4-7) membered monocyclic ring or a fused 8-12 membered bicyclic ring which may be saturated or partially unsaturated, which monocystic or bicyclic ring contains 1 to 4 heteroatoms selected from oxygen, nitrogen, silicon or sulphur. Examples of such monocyclic rings include oxaziridinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1H-3-benzazepine, 4-(benzo[d][1,3]dioxol-5-ylmethyl)piperazin-2-yl, and, tetrahydroisoquinolinyl.

The term 'heterocyclyl substituted with one or more oxygen atoms' refers to a heterocyclyl ring which has one or more oxygen atoms bonded to the ring. It does not mean that the heterocyclyl ring contains one or more oxygen atoms as ring atoms, although in some embodiments, this may be the case. Preferably, the one or more oxygen atoms is bonded to a heteroatom, such as nitrogen or sulphur, in the heterocyclyl ring. An example of a heterocyclyl substituted with one or more oxygen atoms is 1,1-dioxido-1,3-thiazolidinyl.

The terms 'bicyclic ring' and 'fused' in the context of a bicyclic ring refers in connection with this aspect to two rings which are joined together across a bond between two atoms (e.g. naphthalene), across a sequence of atoms to form a bridge (e.g. quinuclidine) or together at a single atom to form a Spiro compound (e.g. 1,4-dioxa-8-aza-spiro[4.5]decane and N,3,3-dimethyl-1,5-dioxaspirol[5.5]undecan-9-yl).

The term '$C_{x-y}$ cycloalkyl' as used herein refers to a saturated hydrocarbon ring of x to y carbon atoms which can be mono, bi or tricyclic. For example, $C_{3-10}$ cycloalkyl refers to a saturated mono, bi or tricyclic hydrocarbon ring of 3 to 10 carbon atoms. Examples of $C_{3-10}$ cycloalkyl groups include cyclopropyl, cyclobutyl, cyclopentyl, cyclohexyl, cycloheptyl, cyclooctyl and adamantyl.

The term 'aryl $C_{x-y}$ alkyl' as used herein refers to an aryl group as defined above attached to a $C_{x-y}$ alkyl as defined above. For example, aryl $C_{1-6}$ alkyl refers to an aryl group attached to a linear or branched saturated hydrocarbon group containing from 1 to 6 carbon atoms. Examples of aryl $C_{1-6}$ alkyl groups include benzyl, phenylethyl, phenylpropyl, phenylbutyl, phenylpentyl and phenylhexyl.

The terms 'heteroaryl $C_{x-y}$ alkyl', 'heterocyclyl $C_{x-y}$ alkyl' and '$C_{x-y}$ cycloalkyl $C_{x-y}$ alkyl' as used herein refers to a heteroaryl, heterocyclyl or $C_{x-y}$ cycloalkyl group as defined above attached to a $C_{x-y}$ alkyl as defined above.

The term '$C_{x-y}$ alkoxy' as used herein refers to an —O—$C_{x-y}$ alkyl group wherein $C_{x-y}$ alkyl is as defined above. Examples of such groups include methoxy, ethoxy, propoxy, butoxy, pentoxy and hexoxy.

The term 'aryl $C_{x-y}$ alkoxy' as used herein refers to an aryl group as defined above attached to a $C_{x-y}$ alkoxy as defined above. For example, aryl $C_{1-6}$ alkoxy refers to an aryl group attached to an alkoxy group containing from 1 to 6 carbon atoms.

The term 'heteroaryl $C_{x-y}$ alkoxy' as used herein refers to a heteroaryl group as defined above attached to a $C_{x-y}$ alkoxy as defined above. For example, heteroaryl $C_{1-6}$ alkoxy refers to a heteroaryl group attached to an alkoxy group containing from 1 to 6 carbon atoms.

The term 'heterocyclyl $C_{x-y}$ alkoxy' as used herein refers to a heterocyclyl group as defined above attached to a $C_{x-y}$ alkoxy as defined above. For example, heterocyclyl $C_{1-6}$ alkoxy refers to a heterocyclyl group attached to an alkoxy group containing from 1 to 6 carbon atoms.

The term '$C_{x-y}$ cycloalkyl $C_{x-y}$ alkoxy' as used herein refers to a $C_{x-y}$ cycloalkyl group as defined above attached to a $C_{x-y}$ alkoxy as defined above. For example, $C_{1-6}$ cycloalkyl $C_{1-6}$ alkoxy refers to a cycloalkyl group containing from 1 to 6 carbon atoms attached to an alkoxy group containing from 1 to 6 carbon atoms.

The term 'aryloxy' as used herein refers to an —O-aryl group. Examples of such groups include phenoxy. The terms 'heteroaryloxy' and 'heterocyclyloxy' as used herein refer to an —O-heteroaryl and —O-heterocyclyl group respectively. The term '$C_{x-y}$ cycloalkyloxy' as used herein refers to an —O—$C_{x-y}$ cycloalkyl group.

The term 'halogen' as used herein refers to a fluorine, chlorine, bromine or iodine atom, unless otherwise specified.

The term '$C_{x-y}$ alkylamino' as used herein refers to a secondary amine group (—NH(R)) of which the R group is selected from a linear or branched saturated hydrocarbon group containing from x to y carbon atoms. Examples of $C_{x-y}$ alkylamino groups include methylamino, ethylamino and propylamino.

The term '$C_{x-y}$ dialkylamino' as used herein refers to a tertiary amine group (—NR(R*)) of which the R and R* groups are each independently selected from a linear or branched saturated hydrocarbon group containing from x to y carbon atoms. Examples of $C_{x-y}$ dialkylamino groups include dimethylamino, methylethylamino and diethylamino.

The term 'substituted $C_{1-6}$ alkyl' used herein with reference to the identity of the various groups identified as R (for example, in the phrase 'wherein R1e and R1f are independently selected from $C_{1-4}$ alkyl, substituted $C_{1-6}$ alkyl, aryl, heteroaryl. $C_{3-8}$ cycloalkyl and heterocyclyl') means that the particular R group (e.g. R1a, R2c, R5e, etc.) can be substituted with one or more groups selected from R', halogen, OH, OR', SH, SR', OCOR', SCOR', NH$_2$, NO$_2$, NHR', NHSO$_2$NH$_2$, NHSO$_2$R', NR'COR", NHC(NH)NH$_2$, NHCOR', NR'R", COR', CSR', CN, COOH, COOR', CONH$_2$, CONHOH, CONHR', CONR'R", CONHOR', C(NOH)NH$_2$, SO$_2$R', SO$_3$H, SO$_2$NH$_2$, SO$_2$NR'R", wherein R' and R" are independently selected from $C_{1-6}$ alkyl, aryl, heteroaryl, $C_{3-8}$ cycloalkyl and heterocyclyl, or R' and R", together with the heteroatom to which they are joined, can form heterocyclyl.

The term 'acyl' as used herein refers to a group selected from:
(1) formyl (i.e. —CHO));
(2) $C_{1-6}$ alkyl carbonyloxy;
(3) $C_{1-6}$ alkyl carbonyl;
(4) $C_{6-10}$ aryl carbonyl;
(5) carboxyl (i.e. —CO$_2$H);
(6) $C_{1-6}$ alkyl carbamoyl;
(7) carbamoyl (i.e. —CONH$_2$; and
(8) $C_{1-6}$ alkoxy carbonyl.

The term '$C_{x-y}$ alkyl carbonyloxy' as used herein refers to an alkyl group wherein $C_{x-y}$ alkyl is as defined herein and at least one methylene group (i.e. —CH$_2$—) is replaced with an ester group (e.g. —CO$_2$—). Examples of $C_{1-6}$ alkyl carbonyloxy groups include ethanoate, propanoate, butanoate, pentanoate, and hexanoate.

The term '$C_{x-y}$ alkyl carbonyl' as used herein refers to an alkyl group wherein $C_{x-y}$ alkyl is as defined herein and at least one methylene group (i.e. —CH$_2$—) is replaced with a carbonyl group (i.e. >C=O). Examples of $C_{1-6}$ alkyl carbonyl groups include methylcarbonyl, ethyl-1-carbonyl, ethyl-2-carbonyl, propyl-1-carbonyl, propyl-2-carbonyl, propyl-3-carbonyl, isopropylcarbonyl, butyl-1-carbonyl, butyl-2-carbonyl, butyl-3-carbonyl, butyl-4-carbonyl, isobutylcarbonyl, tertiarybutylcarbonyl pentylcarbonyl, and hexylcarbonyl.

The term '$C_{x-y}$ aryl carbonyl' as used herein refers to an aryl group wherein $C_{x-y}$ aryl is as defined herein covalently linked to at least one carbonyl group (i.e. >C=O). Examples of $C_{6-10}$ aryl carbonyl groups benzoyl, 1-naphthoyl, and 2-naphthoyl.

The term '$C_{x-y}$ alkyl carbamoyl' as used herein refers to an alkyl group wherein $C_{x-y}$ alkyl is as defined herein and at least one methylene group (i.e. —CH$_2$—) is replaced with an amide group (e.g. —C(O)NR—, where R is a hydrogen atom, a 5- or 6-membered heterocyclyl group, a 5- or 6-membered heteroaryl group, a 3- to 6-membered cycloalkyl group, a $C_{1-6}$ alkyl group, or a $C_{6-14}$ aryl group, preferably a hydrogen atom). Examples of $C_{1-6}$ alkyl carbamoyl groups include ethyl carbamoyl, propyl carbamoyl, butyl carbamoyl, tert-butyl carbamoyl, pentyl carbamoyl, and hexyl carbamoyl.

The term '$C_{x-y}$ alkoxy carbonyl' as used herein refers to an alkyl group wherein $C_{x-y}$ alkyl is as defined herein and at least one methylene group (i.e. —CH$_2$—) is replaced with an ester group (e.g. —OC(O)—), Examples of $C_{1-6}$ alkyl carbonyl groups include ethyl oxycarbonyl, propyl oxycarbonyl, butyl oxycarbonyl, pentyl oxycarbonyl, and hexyl oxycarbonyl.

In a preferred embodiment, the acyl group is selected from:
(1) formyl (i.e. —CHO);
(2) $C_{1-6}$ alkyl carbonyloxy optionally substituted with 1 to 3 groups selected from halogen, hydroxy, and aryl;
(3) $C_{1-6}$ alkyl carbonyl optionally substituted with 1 to 3 groups selected from halogen, hydroxy, and aryl;
(4) $C_{6-10}$ aryl carbonyl optionally substituted with 1 to 3 groups selected from halogen, hydroxy, $C_{1-6}$ alkyl, and $C_{1-6}$ alkoxy;
(5) carboxyl (i.e. CO$_2$H);
(6) $C_{1-6}$ alkyl carbamoyl optionally substituted with 1 to 3 groups selected from halogen, hydroxy, and aryl;
(7) carbamoyl; and
(8) $C_{1-6}$ alkoxy carbonyl optionally substituted with 1 to 3 groups selected from halogen, hydroxy, and aryl.

In a preferred embodiment of the invention, R1 is selected from H and $C_{1-4}$ alkyl. More preferably, R1 is selected from H, methyl and ethyl.

In another preferred embodiment, R2 is selected from aryl, heteroaryl, heterocyclyl, $C_{3-10}$ cycloalkyl, aryl $C_{1-6}$ alkyl, heteroaryl $C_{1-6}$ alkyl, heterocyclyl $C_{1-6}$ alkyl and $C_{3-10}$ cycloalkyl $C_{1-6}$ alkyl, each of which may be substituted or unsubstituted. Preferably, R2 is selected from aryl, heteroaryl, heterocyclyl, and $C_{1-10}$ cycloalkyl each of which may be substituted or unsubstituted.

In a particularly preferred aspect, R2 is selected from fully saturated heterocyclyl, and $C_{5-8}$ cycloalkyl each of which are monocyclic and may be substituted or unsubstituted. For example, R2 may be an unsubstituted cyclopentyl or unsubstituted cyclohexyl, or a fully saturated heterocyclyl, wherein the heterocyclyl ring contains a single heteroatom, such as nitrogen or oxygen. When R2 is heterocyclyl, it is preferably six membered heterocyclyl and the heteroatom in the said heterocyclyl group is at the 4-position relative to the position of attachment of the heterocyclyl group R2 to the urea nitrogen. In this case, the heteroatom is preferably a nitrogen heteroatom which is substituted with a group selected from CN, CONH$_2$, C(NOH)NH$_2$, SO$_2$—$C_{1-4}$ alkyl, SO$_2$-aryl, CO-heteroaryl, CO—$C_{1-4}$ alkyl, COO—$C_{1-4}$ alkyl, $C_{1-4}$ alkyl, aryl $C_{1-4}$ alkyl, heteroaryl $C_{1-3}$ alkyl, heterocyclyl $C_{1-3}$ alkyl, aryl, heteroaryl, and heterocyclyl, wherein the $C_{1-4}$ alkyl may optionally be substituted with OH, CN, COOH, the SO$_2$-aryl may optionally be substituted with a $C_{1-4}$ alkyl or $C_{1-4}$ haloalkyl, the CO-heteroaryl may optionally be substituted with a heteroaryl or halogen, the heteroaryl $C_{1-3}$ alkyl may optionally be substituted with COO—$C_{1-3}$ alkyl, and the heteroaryl may optionally be substituted with one or more halogens. More preferably, the nitrogen heteroatom is substituted with phenyl $C_{1-3}$ alkyl.

In a further preferred embodiment, R6 is selected from monocyclic aryl, monocyclic heteroaryl, and heterocyclyl, each of which may be substituted or unsubstituted. Where R6 is a substituted aryl, said aryl is preferably substituted with one or more groups selected from halogen, R6a, OH, OR6a, $NH_2$, $NO_2$, $NHC(NH)NH_2$, NHR6a, NR6aR6b, $C(NOH)NH_2$, COR6a, COOH, COOR6a, $CONH_2$, CONHOH, $SO_2$R6a, $SO_2$NR6aR6b, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein R6a and R6b are independently selected from $C_{1-6}$ alkyl, substituted $C_{1-6}$ alkyl, aryl, heteroaryl, $C_{3-8}$ cycloalkyl and heterocyclyl, wherein, when the substituent of R6 is $C_{1-6}$ alkyl, substituted $C_{1-6}$ alkyl, aryl, heteroaryl, $C_{3-8}$ cycloalkyl, heterocyclyl or is a group containing one or more of these moieties, each of these moieties may optionally be substituted with one or more groups selected from OR6c, OH, and $CONH_2$, wherein R6c and R6d are independently selected from $C_{1-6}$ alkyl, substituted. $C_{1-6}$ alkyl, aryl, heteroaryl, $C_{3-8}$ cycloalkyl and heterocyclyl, and wherein, when the substituent of R6 is heteroaryl or heterocyclyl, each of these moieties may optionally be substituted with one or more oxygen atoms.

More preferably, R6 is a substituted aryl which is substituted with one or more groups selected from halogen, OH, $C_{1-4}$ alkoxy, $CONH_2$, $C(NOH)N)H_2$, CONHOH, $SO_2$—$C_{1-4}$ alkyl, heterocyclyl, and aryl, wherein the heterocyclyl may optionally be substituted with an oxygen atom and the aryl may optionally be substituted with $CONH_2$.

In an alternative preferred embodiment, R6 is a heterocyclyl which is substituted with an oxygen atom.

In another alternative preferred embodiment, R6 is a monocyclic heteroaryl which is substituted with an oxygen atom.

In another preferred embodiment of the invention, R5 is hydrogen.

In a further preferred embodiment of the invention, R5 is hydrogen or a group selected from:

$C_{1-6}$ alkyl optionally substituted with one or more groups selected from halogen, hydroxy, and $C_{1-6}$ alkoxy optionally substituted with 1 to 3 groups selected from hydroxy, $C_{1-6}$ alkyl, $C_{1-6}$ alkylamino, and $C_{1-6}$ dialkylamino;

aryl optionally substituted with one or more groups selected from halogen, hydroxy, $C_{1-6}$ alkyl, $C_{1-6}$ alkoxy, $C_{1-6}$ haloalkyl, acyl, and aryl optionally substituted with 1 to 3 groups selected from halogen, $C_{1-6}$ haloalkyl, and acyl;

heteroaryl optionally substituted with one or more groups selected from halogen, hydroxy, $C_{1-6}$ alkoxy, acyl, and $C_{1-6}$ alkyl optionally substituted with 1 to 3 groups selected from heterocyclyl and heteroaryl each of which is optionally further substituted with 1 to 3 groups selected from $C_{1-6}$ alkyl, and heteroaryl $C_{1-6}$ haloalkyl;

heterocyclyl optionally substituted with one or more groups selected from halogen, hydroxy, $C_{1-6}$ alkoxy, and acyl; and $C_{3-4}$ cycloalkyl optionally substituted with one or more groups selected from halogen, hydroxy, $C_{1-6}$ alkoxy, and acyl.

Most preferably, R8 is hydrogen, i.e. the aldehyde R8CHO employed is formaldehyde.

According to a second aspect of the present invention, there is provided a process for preparing an imidazolyl intermediate of Formula IIa':

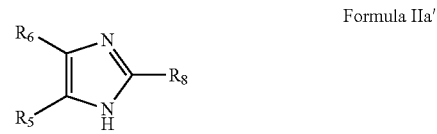

Formula IIa' or a pharmaceutically acceptable salt thereof, the process comprising the oxidation of the derivative of R5 and R6, R6-C(=O)CH$_2$R5, to form a glyoxal intermediate R6-C(=O)(C=O)R5, which is subjected to treatment with ammonium hydroxide and an aldehyde R8CHO to provide the intermediate of Formula IIa', wherein R5, R6, and R8 are as defined above in connection with the first aspect, and wherein, when the intermediate of Formula IIa' is 4-(3-pyridyl)imidazole, the intermediate of Formula IIa' is not extracted from the reaction mixture using dichloromethane.

The process of the second aspect is useful for obtaining the intermediates of Formula IIa'. A process for obtaining an intermediate of this type is described by Cao et al. (see above), However, it has been found that, for extracting other such intermediates from the reaction mixture, DCM is not an efficient solvent. Thus, in certain embodiments of the first and second aspects, it has been found that a solvent comprising butanol, preferably 1-butanol, is a useful extraction solvent. In other embodiments, the aqueous media in the reaction mixture can be evaporated, and the remaining material can be dissolved in a suitable solvent for further processing.

The relevant particular embodiments described above in connection with the first aspect may also be applied, as appropriate, to the second aspect. Thus, in the case of the preparation of the compound of Formula A, R6 is $NH_2$CONH-phenyl, or the nitrophenyl, aminophenyl or amino-protected aminophenyl precursor of this moiety which is subjected to conversion to the $NH_2$CONH-phenyl group after urea formation, and R5 is H, R1 is methyl and R2 is cyclopentyl.

In particular, R5 is preferably hydrogen, and/or R6 is preferably selected from monocyclic aryl, monocyclic heteroaryl, and heterocyclyl, each of which may be substituted with one or more of the substituents defined for R6 above in connection with the first aspect or with $NH_2$CONH—. In addition or alternatively, R8 is preferably hydrogen.

In an embodiment of the second aspect, the resulting intermediate of Formula IIa' is reacted with a carbamoyl halide R1R2NC(=O)Hal to form a urea of Formula IIa or Formula A, as described in the first aspect.

In accordance with a third aspect of the invention, there is provided a compound having the formula R6(C=O)

(C=O)R5, wherein R5 and R6 are as defined above in connection with the first aspect, provided that when R6 is pyridyl, R5 is not H.

The relevant particular embodiments described above in connection with the first and second aspects may also be applied, as appropriate, to the third aspect. For example, R5 may be hydrogen, and/or R6 may be selected from monocyclic aryl, monocyclic heteroaryl, and heterocyclyl, each of which may be substituted with one or more of the substituents defined for R6 above in connection with the first aspect or with $NH_2CONH-$.

In accordance with a fourth aspect of the invention, there is provided a process for preparing a substituted urea compound of Formula A as described above, or a pharmaceutically acceptable salt or derivative thereof, the process comprising the reaction of an intermediate of Formula IIa' as defined above, with a carbamoyl halide of the formula: R1R2NC(=O)Hal, in a solvent consisting essentially of pyridine, wherein R6 is $NH_2CONH$-phenyl, or a nitrophenyl, aminophenyl or amino-protected aminophenyl precursor of this moiety which can be subjected to conversion to the $NH_2CONH$-phenyl group after urea formation, and R5 is H, R1 is methyl and R2 is cyclopentyl, and wherein Hal represents Cl, F, I or Br.

By using pyridine as the solvent for the urea formation reaction in the production of the compound of Formula A, an improvement in yield (potentially greater than 90%) may be achieved. The solvent used for the reaction of the intermediate of Formula IIa' with the carbamoyl halide consists essentially of pyridine. In the context of the present invention, 'consists essentially of pyridine' means that the solvent used for the reaction comprises at least 10% v/v pyridine together with other, preferably miscible, solvents. Such other solvents may comprise, for example, dichloromethane or dimethylformamide. In certain embodiments, the solvent comprises at least 20%, at least 25%, at least 30%, at least 40%, at least 50%, at least 60%, at least 70%, at least 75%, at least 80%, or at least 90% v/v pyridine. Allowing the reaction solvent to contain other solvents means that one or both of the reacting species can be introduced in a solvent other than pyridine, provided that the solvent used for the reaction contains enough pyridine to produce an improvement in yield, as demonstrated by the process described herein. The higher the content of pyridine in the solvent, however, the greater the improvement in yield. The purity of the urea produced may also be enhanced by the pyridine solvent.

In an embodiment of the fourth aspect, the product mixture after urea formation may be further treated with water. In this way, the isolation procedure of the product may be simplified, since the addition of water has been found to promote precipitation of the product from the crude product mixture. Furthermore, this means that the removal of large volumes of pyridine and subsequent solvent swaps (e.g. with heptanes) may be avoided.

In another embodiment of the fourth aspect, the product mixture after urea formation may be further treated with a $C_{5-10}$ alkane or mixtures thereof, preferably a $C_{5-8}$ alkane or mixtures thereof. For example, the $C_{5-10}$ alkane or mixtures thereof may be employed as a solvent in an extraction procedure to purify and isolate the compound of Formula A. In particular, it has surprisingly been found that an antisolvent comprising heptane is especially advantageous in such a treatment and leads to an improved yield of the desired product.

In this context, the term "$C_{5-10}$ alkane" refers to linear or branched alkanes having 5 to 10 carbon atoms. For example, the term "heptane" includes n-heptane and any structural isomers thereof, such as isoheptane (2-methylhexane), 3-methylhexane, 2,2-dimethylpentane, 3-ethylpentane, 2,2,3-trimethylbutane, etc.

In embodiments of the fourth aspect, the urea product is subjected to conversion of R6, where necessary, to the $NH_2CONH$-phenyl group of the compound of Formula A.

'Pharmaceutically acceptable salts' of compounds prepared by the present invention include salts with inorganic bases, salts with organic bases, salts with inorganic acids, salts with organic acids and salts with basic or acidic amino acids. Salts with, acids may, in particular, be employed in some instances. Exemplary salts include hydrochloride salt, acetate salt, trifluoroacetate salt, methanesulfonate salt, 2-hydroxypropane-1,2,3-tricarboxylate salt, (2R,3R)-2,3-dihydroxysuccinate salt, phosphate salt, sulphate salt, benzoate salt, 2-hydroxy-benzoate salt, S-(+)-mandelate salt, S-(−)-malate salt, S-(−) pyroglutamate salt, pyruvate salt, p-toluenesulfonate salt, 1-R-(−)-camphorsulfonate salt, fumarate salt and oxalate salt. The compound prepared by the present invention may be in either solvate (e.g. hydrate) or non-solvate (e.g. non-hydrate) form. When in a solvate form, additional solvents may be alcohols such as propan-2-ol.

'Pharmaceutically acceptable esters' of compounds of the invention are derivatives in which one or more carboxyl (i.e. —C(O)OH) groups of the said compounds are modified by reaction with an alcoholic moiety U—OH so as to yield —C(O)OU groups, wherein U may be $C_{1-18}$ alkyl (e.g. $C_{1-6}$ alkyl), aryl, heteroaryl, $C_{3-8}$ cycloalkyl or combinations thereof.

'Pharmaceutically acceptable derivatives' of the compound of Formula A prepared by the invention are derivatives in which one or more groups of the compound is modified by reaction with another molecule. For example, derivatives of the compound of Formula A include the modification of the $NH_2$ group as shown in the following Scheme.

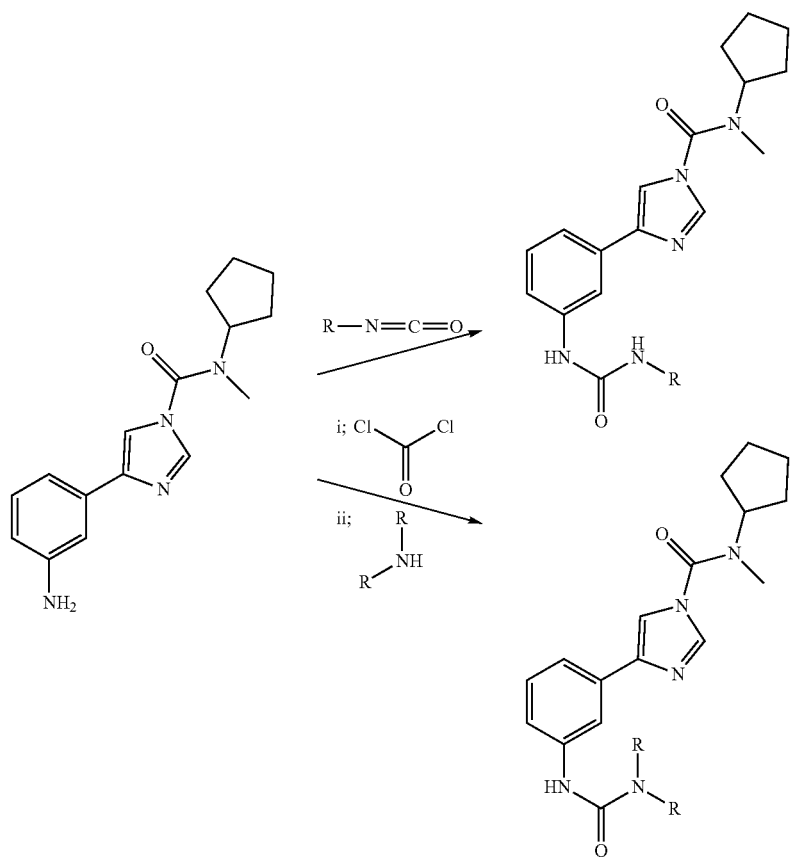

For example, derivatives include the products of reaction of the $NH_2$ group of 4-(3-aminophenyl)-N-cyclopentyl-N-methyl-1H-imidazole-1-carboxamide with R—N=C=O isocyanate (see R. G. Arnold, J. A. Nelson, J. J. Verbanc: Recent Advances in Isocyanate Chemistry *Chemical Reviews*, 57(1), 47-76, 1957 and the references therein) to form NH—(C=O)—NHR derivative, or with Cl—(C=O)—Cl and $NHR_2$ (see H. Babad, A. G. Zeiler: Chemistry of Phosgene *Chemical Reviews*, 73(1), 75-91, 1973 and the references therein) to form NH—(CO)—$NR_2$, in which R may be $C_{1-18}$ alkyl (e.g. $C_{1-6}$ alkyl), aryl, heteroaryl, $C_{3-8}$ cycloalkyl or combinations thereof. Pharmaceutically acceptable derivatives can be produced in any suitable way and methods for their production would be apparent to one skilled in the art based on well known principles in organic and medicinal chemistry (for example, suitable methods are disclosed in Vogel's Textbook of Practical Organic Chemistry, $5^{th}$ edition, Longman, 1989).

General methods for the preparation of salts, esters and derivatives are well known to the person skilled in the art. Pharmaceutical acceptability of salts, esters and derivatives will depend on a variety of factors, including formulation processing characteristics and in vivo behaviour, and the skilled person would readily be able assess such factors having regard to the present disclosure.

Where compounds prepared by the invention may exist as alternative tautomeric forms (e.g. keto/enol, amide/imidic acid), the invention relates to the individual tautomers in isolation, and to mixtures of the tautomers in all proportions.

The relevant particular embodiments described above in connection with the first to third aspects may also be applied, as appropriate, to the fourth aspect.

In a fifth aspect of the invention, there is provided a process for the synthesis of N-methylcyclopentylamine hydrochloride, the process comprising the reaction of cyclopentylamine with a chloroformate, carried out in 2-methyltetrahydrofuran as the solvent, so as to form a cyclopentylcarbamate, followed by reduction of the cyclopentylcarbamate and acidification with Ha to N-methylcyclopentylamine hydrochloride.

This process can be used to efficiently produce N-methylcyclopentylamine hydrochloride, a key intermediate in the preparation of the compound of Formula A. Although such an intermediate may be prepared by other means (for example, reductive amination), the present process provides high yield and good quality product. Surprisingly, it has been found that the use of 2-methyltetrahydrofuran as the solvent in the cyclopentylcarbamate formation step leads to an improved yield. The use of 2-methyltetrahydrofuran also avoids the need to use methyl tert-butyl ether in the work-up procedure.

In embodiments, the cyclopentylcarbamate formation is conducted in basic conditions, for example, NaOH (e.g. 3M). The chloroformate used for this step may, for example, be $C_{1-4}$, such as ethyl, chloroformate. The reduction step may be conducted using lithium aluminium hydride (LAH), in a solvent such as tetrahydrofuran or 2-methyltetrahydrofuran. As such, the two step process can be advantageously telescoped into a single procedure, without requiring purification of the cyclopentylcarbamate product.

Furthermore, it has been found that this procedure is effective even when a reduced amount of lithium aluminium hydride is used. In particular, it is preferable that 1.5 to 4 equivalents of lithium aluminium hydride is employed, more preferably 2 to 3 equivalents, most preferably approximately 2.5 equivalents.

For isolation of the product, it is convenient to add HCl (e.g. concentrated) so as to form the HCl salt of N-methylcyclopentylamine. Furthermore, the solvent system employed for isolation is preferably dichloromethane/methyl tert-butyl ether.

The N-methylcyclopentylamine hydrochloride produced according to this process may subsequently be used for the preparation of a compound of Formula A, using any of the processes for preparation of that compound described herein.

The invention will now be described in more detail by way of example only:

1. Synthetic Methodologies

The methods used for synthesis of the compounds described are illustrated by the schemes below. All compounds and intermediates were characterised by nuclear magnetic resonance (NMR). The starting materials and reagents used in preparing these compounds are available from commercial suppliers or can be prepared by methods obvious to those skilled in the art.

Abbreviations:
NMT=not more than
NLT=not less than
LOD=loss on drying
SM=starting material Room temperature in the following schemes means the temperature ranging from 20° C. to 25° C.

2. General Scheme for synthesis of N-cyclopentyl-N-methyl-4-(3-ureidophenyl)-1H-imidazole-1-carboxamide (Compound of Formula A)—Comparative

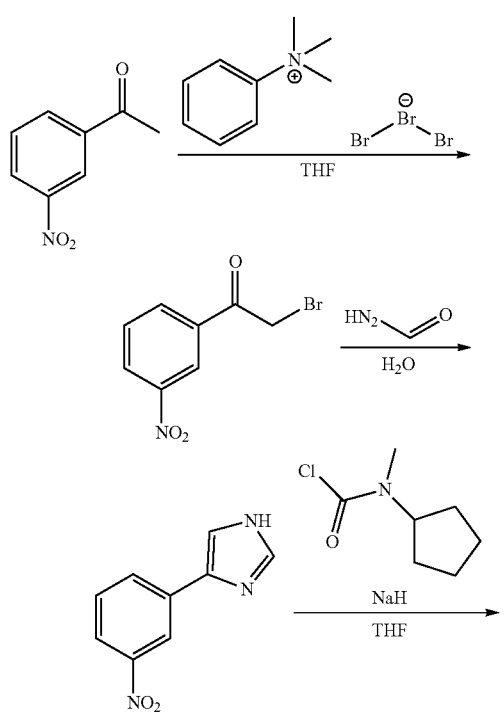

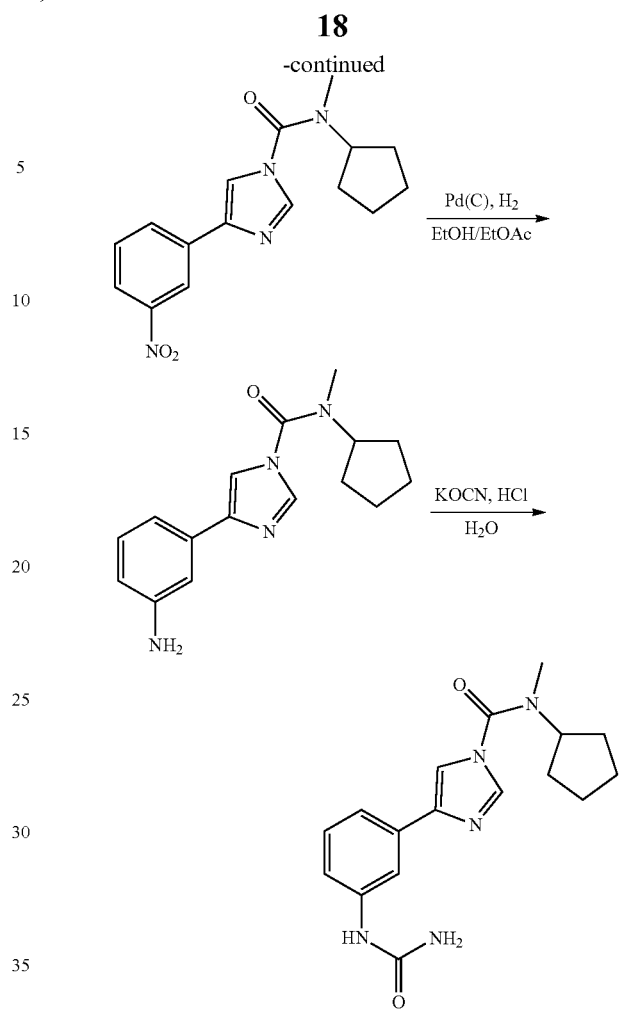

2-Bromo-1-(3-nitrophenyl)ethanone

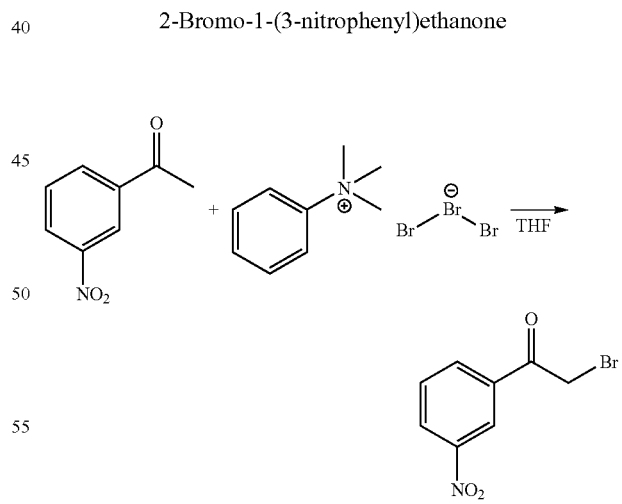

A solution of phenyltrimethylammonium tribromide (50.1 g, 133 mmol) in THF (200 mL) was added dropwise to a stirred solution of 1-(3-nitrophenyl)ethanone (20 g, 121 mmol) in THF (200 mL) at room temperature. The reaction mixture was allowed to stir at room temperature for 1 h. The white suspension was filtered and the filter cake was washed with THF, the filtrate was evaporated in vacuum to give a yellow oil. The residue was then dissolved in EtOAc and was washed with water. The organic layer was dried (MgSO$_4$) and evaporated in vacuum to give a yellow oil that solidified into a yellow solid. Solid recrystallised from isopropanol and final product was isolated as an off-white solid. 2-Bromo-1-(3-nitrophenyl)ethanone (20.5 g, 70% yield).

($^1$H, 600 MHz, 20° C., CDCl$_3$) $\delta_H$: 8.83 (1H, t, J=2 Hz), 8.49 (1H, ddd, J=1.0, 2.3, 8.2 Hz), 8.34 (1H, ddd, J=1.0, 1.7, 7.8 Hz), 7.75 (1H, t, J=8.1 Hz), 4.49 (2H, s).

($^{13}$C, 150 MHz, 20° C., CDCl$_3$) $\delta_C$:189.3, 148.5, 135.1, 134.4, 130.2, 128.1, 123.8, 29.9.

Melting point (mp): 90-91° C.

4-(3-Nitrophenyl)-1H-imidazole

Water ((8 mL) was added to a stirred suspension of 2-bromo-1-(3-nitrophenyl)ethanone (57.1 g, 234 mmol) and formamide (116 mL, 2.9 mol). The mixture was allowed to stir at 140° C. for 5 h. The brown residue was poured into 300 mL of water and the resulting precipitate was separated by filtration and was washed with a 1M HCl solution. The filtrate was basified with 50% NaOH and the resulting yellow precipitate was separated by filtration and was washed with water. The solid was dried and then recrystallised from isopropanol. 4-(3-Nitrophenyl)-1-H-imidazole (7.05 g, 44% yield).

($^1$H, 600 MHz, 20° C., DMSO) $\delta_H$: 12.37 (1H, s, br), 8.58 (1H, mt, J=2.0 Hz), 8.21 (1H, ddd, J=1.0, 1.6, 7.8 Hz), 8.02 (1H, ddd, J=1.0, 2.5, 8.2 Hz), 7.88 (1H, dd, J=1.2 Hz), 7.79 (1H, dd, J=1.1 Hz), 7.64 (1H, t, J=8.1 Hz).

($^{13}$C, 150 MHz, 20° C., DMSO) $\delta_C$: 148.4, 137.9, 136.8, 136.6, 130.5, 130.0, 120.5, 118.3, 114.6.

Melting point: 221° C. (dec.)

Cyclopentyl(methyl)carbamie Chloride

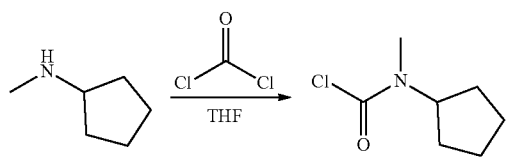

A solution of N-methylcyclopentylamine (10 g, 101 mmol) in THF (126 mL) was added dropwise to phosgene (63.7 mL, 121 mmol) at 0° C. to give a white suspension. The reaction mixture was allowed to stir at room temperature for 1 h. The solution was poured into ice. The organic layer was diluted with EtOAc, was separated washed with 1M HCl, dried (MgSO$_4$) and evaporated in vacuum to give a clear mobile oil. Cyclopentyl(methyl)carbamic chloride (13.1 g, 80% yield).

($^1$H, 600 MHz, 20° C., CDCl$_3$) $\delta_H$: 4.65 (1H, m), 3.0, 2.93 (3H, 2 singlets), 1.92 (2H, m), 1.73 (2H, m), 1.59 (4H, m).

($^{13}$C, 150 MHz, 20° C., CDCl$_3$) $\delta_C$: 149.7, 149.3, 61.1, 59.5, 33.1, 31.1, 28.8, 28.5, 24.0.

N-Cyclopentyl-N-methyl-4-(3-nitrophenyl)-1H-imidazole-1-carboxamide

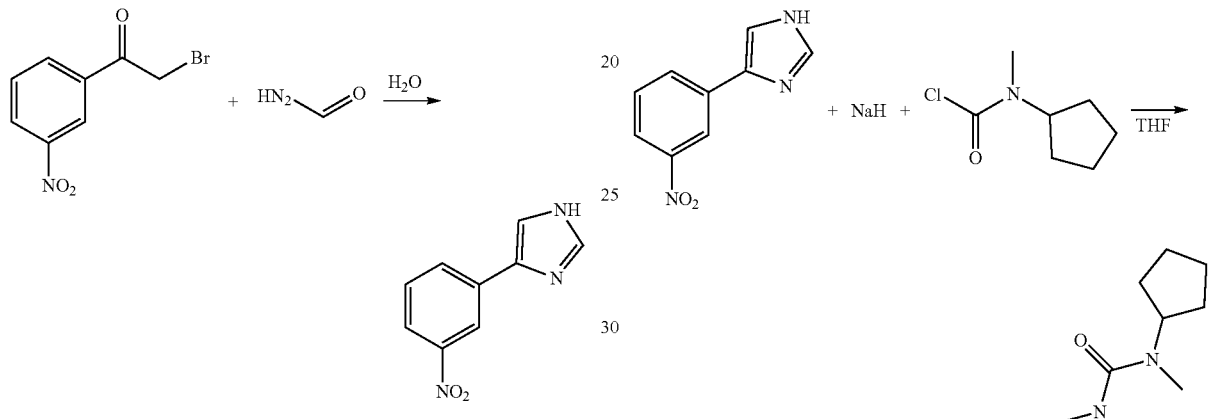

Sodium hydride (5.1 g, 127 mmol) was added portionwise to a stirred suspension of 4-(3-nitrophenyl)-1H-imidazole (20 g, 106 mmol) in THF (500 mL) at 0° C. The yellow suspension turned into a deep red suspension. The mixture was allowed to stir at room temperature for 30 minutes before adding a solution of cyclopentyl(methyl)carbamic chloride (25.6 g, 159 mmol) in THF (26 mL). The suspension was then allowed to stir at room temperature for 2 h. Water was added at 0° C. and the THF was evaporated. The organic residue was extracted with DCM, the organic layer was separated, dried (MgSO$_4$) and evaporated in vacuum to give a beige solid. The solid was triturated with isopropanol. N-Cyclopentyl-N-methyl-4-(3-nitrophenyl)-1H-imidazole-1-carboxamide (25.18 g, 76% yield).

($^1$H, 600 MHz, 20° C., CDCl3) $\delta_H$: 8.63 (1H, mt, J=2.0 Hz), 8.16 (1H, ddd, J=1.0, 1.6, 7.8 Hz), 8.14 (1H, ddd, J=1.0, 2.3, 8.2 Hz), 7.96 (1H, d, J=1.3 Hz), 7.65 (1H, dd, J=1.3 Hz), 7.58 (1H, t, J=8.1 Hz), 4.45 (1H, m), 3.03 (3H, s), 1.98 (2H, m), 1.80 (2H, m), 1.73 (2H, m), 1.66 (2H, m).

($^{13}$C, 150 MHz, 20° C., CDCl$_3$) $\delta_C$: 151.3, 148.7, 140.1, 137.3, 134.9, 134.9, 129.7, 122.1, 119.9, 114.6, 59.4, 31.3, 28.9, 24.4.

Melting point: 121-122° C.

4-(3-Aminophenyl)-N-cyclopentyl-N-methyl-1H-imidazole-1-carboxamide

N-Cyclopentyl-N-methyl-4-(3-ureidophenyl)-1H-imidazole-1-carboxamide (Compound of Formula A)

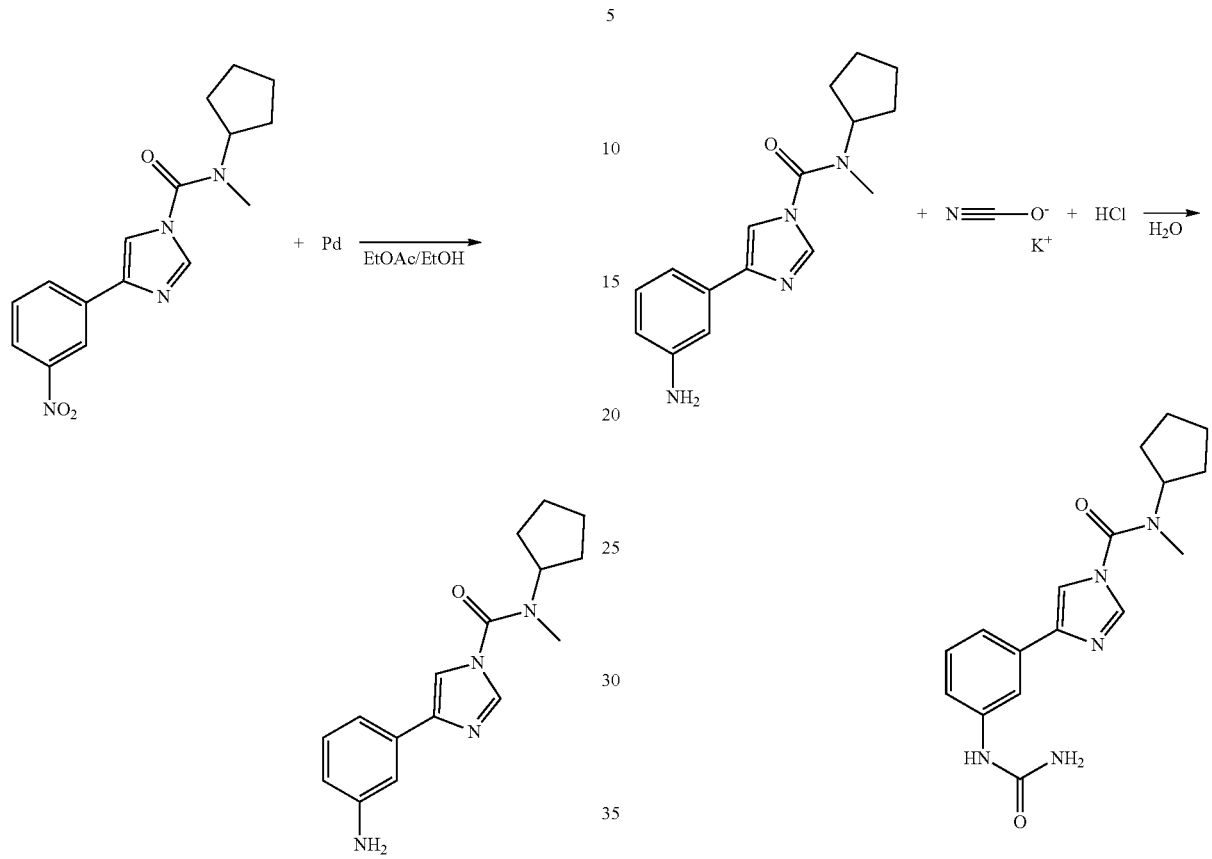

A mixture of Ethyl acetate (160 mL) and EtOH (160 mL) was added to wet Pd/C (0,846 g, 0.795 mmol) under and atmosphere of argon. To this was added N-cyclopentyl-N-methyl-4-(3-nitrophenyl)-1H-imidazole-1-carboxamide (5 g, 15.91 mmol) portionwise and the suspension was allowed to stir at room temperature overnight under and atmosphere of hydrogen. The mixture was flushed with argon and filtered trough celite and the celite was washed with DCM. The filtrate was evaporated in vacuum to give a clear oil that solidified into a colourless solid. The solid was recrystallised from isopropanol. 4-(3-Aminophenyl)-N-cyclopentyl-N-methyl-1H-imidazole-1-carboxamide (3.62 g, 80% yield).

($^1$H, 600 MHz, 20° C., DMSO) $\delta_H$: 8.06 (1H, d, J=1.3 Hz), 7.77 (1H, d, J=1.1 Hz), 7.08 (1H, t, J=1.9 Hz), 7.0 (1H, t, J=7.8 Hz), 6.98 (1H, md, J=7.7 Hz), 6.45 (1H, ddd, J=1.2, 2.3, 7.7 Hz), 5.07 (2H, s), 4.37 (1H, in), 2.92 (3H, s), 1.87 (2H, m), 1.68 (4H, m), 1.53 (2H, m).

($^{13}$C, 150 MHz, 20° C., DMSO) $\delta_C$: 11.2, 148.8, 141.4, 137.3, 133.8, 129.0, 113.7, 112.9, 112.8, 110.4, 58.4, 31.2, 28.2, 24.0.

Melting point: 108-109° C.

Potassium cyanate (0.445 g, 5.49 mmol) was added portionwise to a stirred solution of 4-(3-aminophenyl)-N-cyclopentyl-N-methyl-1H-imidazole-1-carboxamide (1.3 g, 4.57 mmol) in a mixture of 2N hydrogen chloride (2.286 mL, 4.57 mmol) in Water (4 mL) at 0° C. The mixture was allowed to stir at room temperature for 24 h. Potassium cyanate (0.220 g, 2.74 mmol) was added and the mixture was allowed to stir at room temperature for another night. Water was added and the organic layer was diluted with a mixture of DCM/isop 7:3. The organic layer was separated and was washed with a 1N HCl aqueous solution. The organic layer was separated, dried (MgSO$_4$) and evaporated in vacuum to give a colourless foam. The product was purified by column chromatography (silica, DCM/MeOH 5%, 10%) and was isolated as a colourless solid. The solid was recrystallised from EtOH at 0° C. N-Cyclopentyl-N-methyl-4-(3-ureidophenyl)-1H-imidazole-1-carboxamide (0.403 g, 26% yield).

The compounds of the invention above were characterised by melting point and NMR as detailed below. NMR spectra were recorded on a Bruker Avance DPX400 spectrometer with solvent used as internal standard. 13C spectra were recorded at 100 MHz and 1H spectra were recorded at 400 MHz. Data are reported in the following order: approximate chemical shift (ppm), number of protons, multiplicity (br, broad; d, doublet; m, multiplet; s, singlet; t; triplet) and coupling constant (Hz).

Compound of Formula A. (melting point: 204° C.).

($^{13}$C, 150 MHz, 20° C., DMSO) $\delta_C$: 156, 151.1, 140.9, 140.8, 137.5, 133.7, 128.9, 117.9, 116.6, 114.2, 114.2, 58.4, 31.2, 28.2, 24.

($^1$H, 600 MHz, 20° C., DMSO) $\delta_H$: 8.55 (1H, s), 8.09 (1H, d, J=1.2 Hz), 7.86 (1H, d, J=1.2 Hz), 7.85 (1H, t, J=1.8 Hz), 7.35 (1H, md), 7.34 (1H, md), 7.22 (1H, t, J=7.8 Hz), 5.84 (2H, s), 4.36 (1H, m), 2.93 (3H, s), 1.87 (2H, m), 1.69 (4H, m), 1.54 (2H, m).

3. Synthesis of Intermediate of Formula IIa' Via Glyoxal Intermediate

This illustrates the production of an intermediate of Formula IIa' which is useful for preparing the compound of Formula A.

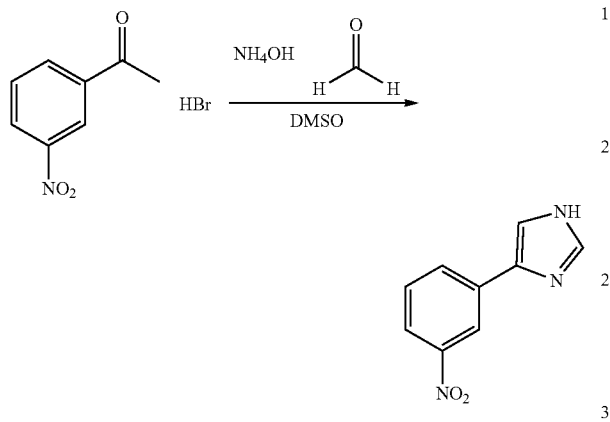

Procedure

To a solution of 1-(3-nitrophenyl)ethanone (50 g, 303 mmol) it DMSO (150 ml) at 20° C. was added dropwise hydrogen bromide (48%, 86 ml, 757 mmol) over 30 minutes keeping internal temperature below 30° C. Note: the addition is exothermic. The reaction mixture was heated to 70° C. (internal temperature) until DMS distillation ceased (around 1 h)

The orange solution (Sol 1) was cooled and discharged in an erlenmeyer.

In a beaker, ammonium hydroxide (337 ml, 2422 mmol) was cooled to 5° C. (ice bath) and the formaldehyde (37%, 54.1 ml, 727 mmol) was added dropwise over 20 minutes keeping internal temperature below 10° C. The resulting clear solution was charged into a 1 L jacketed laboratory reactor. The solution was cooled to 5° C. Sol 1 was then added dropwise over 1h30 keeping the internal temperature below 8° C.

The resulting yellow slurry was stirred at 5° C. overnight and then warmed to 25° C. The yellow slurry become green at room temperature. The slurry was filtered, and the green cake was washed with water (excess), followed by diethylether. NMR of wet solid showed impure product. The solid was then suspended in 3M HCl aqueous solution and was stirred for 1 h at room temperature. The suspension was filtered and the solid was washed with water. The aqueous filtrate was then basified by addition of NaOH until pH 9 was reached. A yellow suspension was obtained. The slurry was stirred, then filtered. The yellow solid was washed with water, then dried by suction. The resulting solid was then dried under vacuum until constant weight. The product (20.29 g) was obtained as yellow solid in 39% yield.

The resulting material can then be used for urea formation, followed by conversion of the nitro group, as described above, to yield the compound of Formula A.

Further details of this approach to producing the imidazole of Formula IIa' are as follows:

In Cao et al (above), they extracted the target pyrido imidazole from the reaction mixture with DCM. In certain instances, this was found not efficient. In some embodiments, this was therefore altered to 1-butanol. While this worked well, it was also decided to evaporate off the aqueous media and replace it with pyridine. Residual DMSO and NH$_4$Br being present in the evaporation residue do not cause interference with carbamoyl chloride for imidazole carbamoylation. The carbamoylation can be conducted at ambient temperature. Raising the temperature to 50° C. should shorten the processing time.

Representative Procedure Illustrating Glyoxal Approach to Alternative Imidazole and Resulting Urea Compound

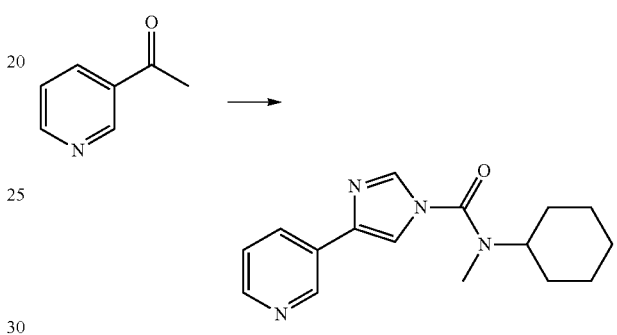

A solution of 3-acetyl pyridine (2.55 gr; 20.41 mmol; 97%) in 6 ml DMSO was cooled by cold water bath. To this solution 8 ml of 48% HBr was added dropwise. When the addition was complete, the apparatus is set to downward distillation and the mixture was warmed to 70 C by water bath. Dimethyl sulfide starts to distill within a few minutes. The reaction is complete in 2 hrs. The mixture was then cooled by cold water and added to an ice cold mixture of 20 ml 25% ammonia solution and 6 ml 35% formaldehyde solution. The mixture was stirred for 1 hr in the ice-bath then it was vacuum evaporated at 70 C, at 35 mbar. The residue was suspended in 10 ml pyridine and the distillation was continued. When no more pyridine distilled, further 10 ml pyridine was added and the mixture was concentrated to obtain a red suspension. 10.4 ml pyridine was added and the suspension was cooled by ambient water bath. 4.1 ml (25.11 mmol; 98%) of N-cyclohexyl-N-methyl carbamoyl chloride was then added and was stirred overnight at ambient temperature. The mixture was then subjected to vacuum evaporation to distill off most of the pyridine. It was then cooled and a mixture of 10 ml 25% ammonia and 20 ml deionised water was added while cooled by ice-water bath for 1 hr. The suspension was filtered, the filter-cake was washed with plenty of DI water to give the target compound as beige solid. Dry weight 3.503 gr (60.3%).

4. Synthesis Towards Compound of Formula A Via Carbamoylation of Imidazole Intermediate of Formula IIa'

In Example 2 above, THF is used as solvent for the urea formation reaction between the imidazole and the cyclopentyl(methyl)carbamic chloride. It has been found that an improved yield may be obtained by using a solvent consisting essentially of pyridine.

To a solution of 4-(3-nitrophenyl)-1H-imidazole (1 wt, 1 eq) in Pyridine (9 vol) was charged N-methylcyclopentylcarbamoyl chloride (1.2 eq). The dark suspension is heated to 90° C. and stirred at that temperature for not more than 1 hour. After 1 hour the reaction is checked for IPC (SM<3.0%). The reaction mixture is concentrated under vacuum until a final volume ~2 vol. Heptane is charged (10 vol) and the mixture is concentrated under vacuum until a final volume ~4 vol. Heptane is charged (5 vol) and the mixture stirred at r.t. for 30 minutes. The suspension is filtered and the cake is washed with water (15 vol) and heptane (2 vol). The wet material is dissolved in refluxing IPA (28.5 vol) and decolorizing charcoal is charged (0.33 wt). After stirring for not more than 30 min at reflux, charcoal is filtered off and the mixture concentrated until a final volume of ~5 vol. After overnight stirring at r.t. filter the suspension and wash the cake with IPA (1 vol). The light beige solid is dried under vacuum at not more than 45° C. until loss on drying <1.0%.

The yield was approaching 90%, and the purity around 98%. The resulting nitro compound can be converted to the compound of Formula A, for example as described above.

5. Larger Scale Synthesis of Compound of Formula A

An exemplary and improved synthesis of the compound of Formula A is provided below.

Stage 1—Bromination

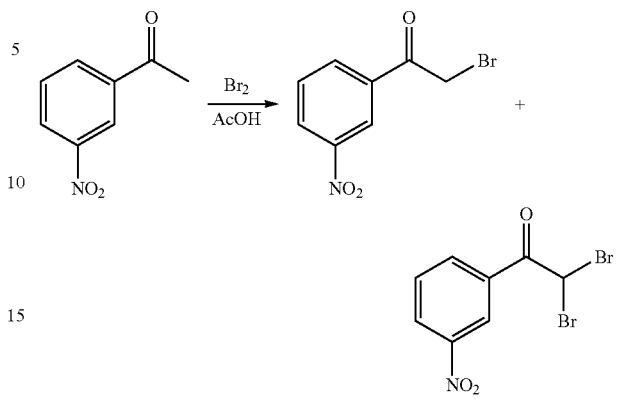

Batch size: 600 g
Molar yield: 61.1%
Quality range: 95.2% area by HPLC

To a solution of 3-Nitroacetophenone (1 wt, 1 eq) in Acetic acid (10 vol) is charged over a period of NLT 8 hours (maintaining the temperature below 25° C.) a solution of bromine (0.37 vol, 1.17 eq). After stirring 18 h at a temperature of 25° C., the reaction progress is checked. After reaction completeness cold water (12 vol) is charged, form-

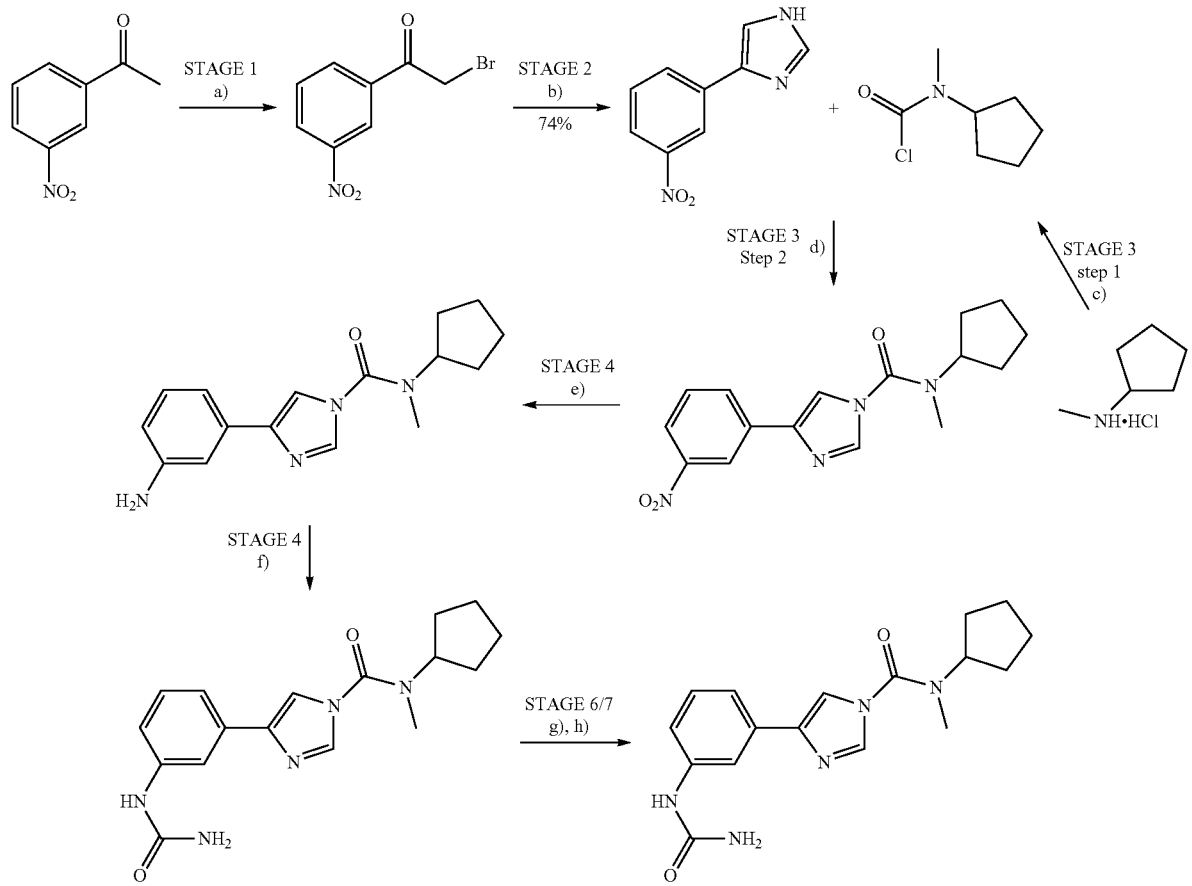

a) AcOH, 1.08 eq Br$_2$; b) Formamide, 140° C.; c) DCM, 0.4 eq Triphosgene, Na$_2$CO$_3$; d) Pyr, 90° C.; e) 10% Pd/C 50% wet, ammonium formate-THF/MeOH; f) AcOH, 2.5 eq KOCN; g) recryst AcOH/H$_2$O; h) EtOH slurry ing a white precipitate. The suspension is stirred for an additional hour at 15° C. and then filtered. The cake is washed with water (4.5 vol). The product is dried under vacuum at a temperature NMT 45° C. until LOD<1.0%. Addition of 2 vol of ice/water into the mother liquors promoted the precipitation of the bis-brominated acetophenone.

Stage 2—Bredereck Reaction

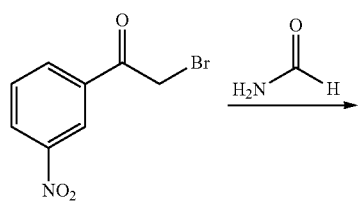

Batch size: 530 g
Molar yield: 74%
Quality range: 99.6% area by HPLC

A solution of the bromoacetophenone (1 wt, 1 eq) in formamide (5 vol) is heated to 140° C. over a period of 3 h (linear ramp) and stirred at this temperature during a period of NLT 6 hours, after which progress is checked. When reaction is complete the mixture is cooled to 10° C. Filter solids and wash with water (1.3 vol) then with 2M HCl (2.8 vol). Basify mother liquors with 50% wt NaOH until pH~14. Filter and wash cake with water (1 vol). The product is dried under vacuum at temperature NMT 45° C. until LOD<1.0%. The material obtained in this way constitutes the main batch. A second minor batch of material was isolated from the formamide mother liquors after dilution with water (4 vol), 2M HCl (1.3 vol) then filtered. The resulting mother liquors were then basified with NaOH (until pH~14). The solids were filtered and washed with water (1 vol). The product was then dried under vacuum at temperature NMT 45° C. until LOD<1.0%. The lower temperature and lower amount of formamide compared to a previous process did not comprise the overall yield, and there was a subsequent reduction in the overall solvent volumes required during the work-up procedure. A second batch of product was also isolated from the mother liquors of formamide.

Stage 3—Step 1—Carbamoylation

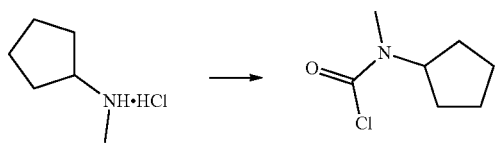

Batch size: 74 g
Molar yield: 100%
Quality range: >95% by NMR

To a suspension of N-Methyl cyclopentyl amine hydrochloride (1 wt, 1 eq) in dichloromethane (5 vol) was added solid Na$_2$CO$_3$ (1.5 eq) and the resulting mixture stirred at rt for 1 h. The suspension was then filtered and the solids washed with dichoromethane (1 vol). The mother liquors were combined and used as such (Sol 2). A solution of Triphosgene (1.2 wt, 0.4 eq) in DCM (10 vol) is cooled to 0-5° C. and stirred over a period of NMT 10 minutes. Sol 2 is charged maintaining the reaction temperature below 10° C. After the amine solution addition charge Na$_2$CO$_3$ (2.14 wt, 2 eq) and allow to warm to r.t. After stirring 2 hours the reaction mixture is filtered and the cake is washed with DCM (2 vol). After concentration to dryness the yellow oil obtained is used in the next step without further treatment.

Stage 3—Step 2—Urea Formation

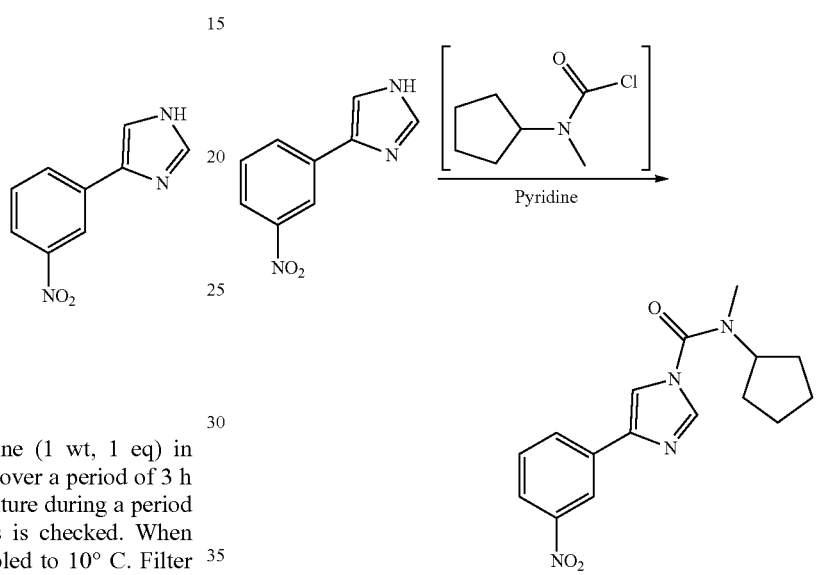

Batch size: 88 g
Molar yield: 92%
Quality range: >99% by HPLC

To a solution of the imidazole (1 wt, 1 eq) in Pyridine (9 vol) was added cyclopentyl(methyl)carbamic chloride (1.23 eq). The dark suspension is heated to 90° C. and stirred at that temperature for NMT 4 hours. After this time the reaction progress is checked (SM<3.0%). Water (10 vol.) is charged and solids filtered and washed with water (4.6 vol) followed by heptanes (4.6 vol). The light beige solids were dried under vacuum at NMT 45° C. until LOD<1.0%. The Urea formation took place in very good conversion (92%), mainly due to a simplified isolation procedure based on the precipitation of the product from the crude mixture by the addition of water. Thus, removal in vacuo of large volumes of pyridine and subsequent solvent swaps with heptanes were avoided.

Stage 4—Nitro Reduction

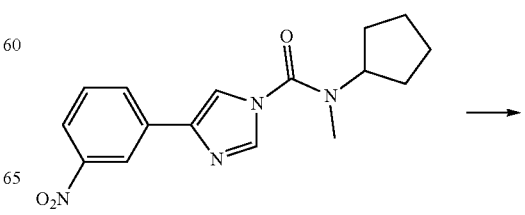

-continued

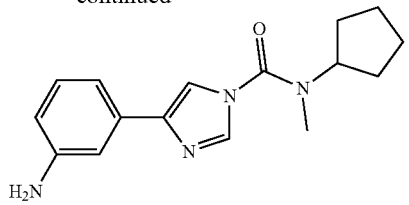

Batch size: 200 g
Molar yield: 96%
Quality range: >99% by HPLC

To a solution of N-cyclopentyl-N-methyl-4-(3-nitrophenyl)-1H-imidazole-1-carboxamide (1 wt, 1 eq) in THF (5 vol) and MeOH (1 vol) was added 10% palladium on charcoal (0.02 eq, 0.07 wt). The reaction was heated to 25° C. prior to addition of ammonium formate (4 eq, 0.8 wt). After 1 h at this temperature, heat the reaction to 28° C. and leave stirring for NLT 18 h. Check progress by HPLC analysis (SM<0.1%). Once complete, dilute mixture with THF (2 vol) followed by EtOAc (5 vol). Filter mixture through a pad of celite and concentrate the combined mother liquors to 5 vol. Charge Isopropyl acetate (3 vol) and distil mixture to 5 vol. Add isopropyl actetate (1 vol) followed by heptane (3 vol). Wash the resulting solids with Heptane/iPrOAc (2 vol:1 vol) and dry in a vacuum at 45° C. until LOD NMT 1%.

Stage 5—Urea Formation

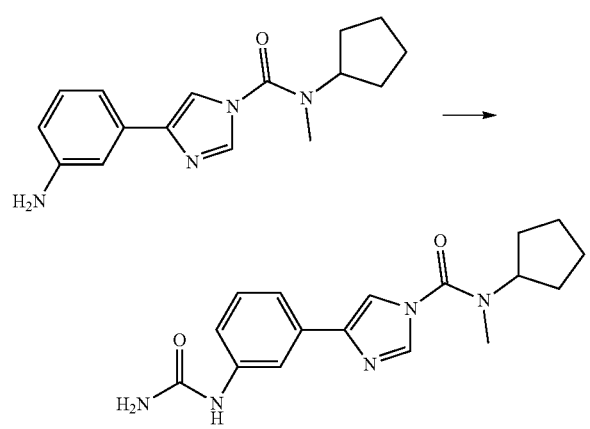

Batch size: 65 g
Molar yield: assume quantitative
Quality range: 94% by HPLC

The aniline is dissolved in AcOH (7 vol) at room temperature. After all solids have dissolved add water (4 vol). Cool the reaction mixture to 0° C. prior to addition of a solution of potassium cyanate (0.71 wt, 2.5 eq) in water (4 Vol). Check conversion by HPLC. The resulting solution is stirred at 0° C. until completion (SM<0.1%). Warm mixture to rt slowly. Within 1 h, the precipitation of the product occurred. To the resulting slurry is added water (11 vol). The beige suspension is then aged for 1 h at room temperature then filtered. The beige solid is washed with water (7 vol), dried under vacuum oven until LOD<1.5%. The relatively swift addition rate of potassium cyanate and/or the low reaction temperature seemed to favour urea formation, and limited the amount of impurities in the crude reaction mixture.

Stage 6/7—Recrystallization and Final Slurry

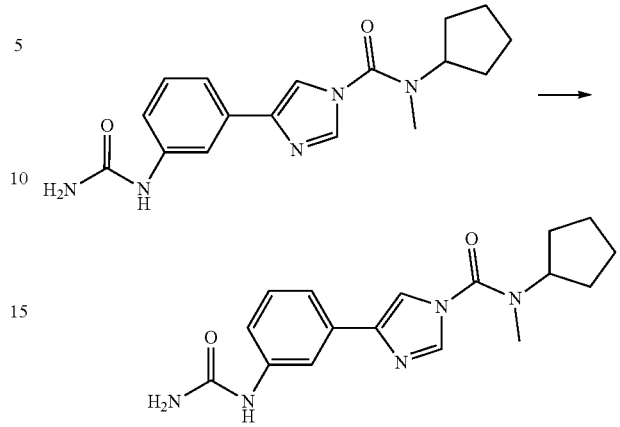

Batch size: 180 g
Molar yield: Estimated 60% molar yield over 2 stages
Quality range: 99.2% by HPLC To a solution of the compound of Formula A (1 wt) in acetic acid (4 vol) at room temperature was added drop-wise water (4 vol) over 30 minutes. After having seeded, water (2 vol) was added and the slurry was aged at room temperature for 1 b then filtered. The beige solid is washed with water (3 vol), dried in a vacuum oven at 45° C. for NLT 18 h. The off beige solid is then dissolved in acetic acid (4 vol) at room temperature and water (4 vol) was added drop wise over 30 minutes. To the solution was then added seeding material, followed by water (2 vol). The resulting slurry was stirred at room temperature for at least 1 h. The solid is filtered, washed with water (6 vol), dried in a vacuum oven at 45° C. until LOD is <1.5%. After drying for 48 h and although LOD (115° C.)=0.49%, the sample still contained AcOH (1.3% wt, as determined by 1H NMR). To remove the traces of acetic acid the solids were suspended in EtOH (4.2 vol) and heated to 50° C. for NLT 4 h. The mixture was cooled to rt and the solids stirred at this T for 30 min prior to filtration in vacuo. The material was then dried in vac oven at 45° C. until LOD<1%. The final slurry with EtOH therefore provided the product in a good level of purity. As such, the present invention therefore provides, in an embodiment, a process for preparing the compound of Formula A in which the compound is recrystallised from acetic acid, preferably with subsequent treatment of the solid using ethanol to remove residual acetic acid.

6. Synthesis of N-methylcyclopentylamine Hydrochloride

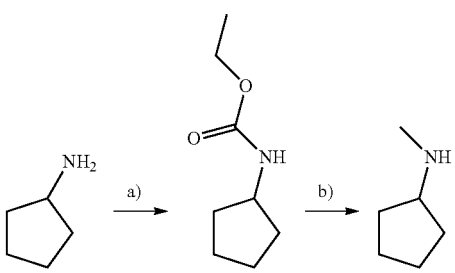

a) EtOCOCl, NaOH; b) LiALH$_4$, ref., HCl

Step 1: Formation of Ethyl Carbamate

To a solution of cyclopentylamine (58.1 ml, 587 mmol) in 2-MeTHF (200 mL) at 0° C. were added respectively 3M sodium hydroxide (300 ml, 900 mmol) and dropwise ethyl chloroformate (67.3 ml, 705 mmol) over 30 minutes. The resulting biphasic mixture was stirred at room temperature until completion. The reaction mixture was diluted with 2-MeTHF (150 mL). The resulting mixture was stirred at room temperature for 10 minutes and then allowed to separate. The organic layer was back extracted with 2-MeTHF (100 mL). The combined organic layers were washed with water (5 vol), 0.5M HCl (3 vol) and then water, then concentrated under reduced pressure. Ethyl cyclopentylcarbamate (100 g) was obtained as colorless oil (NMR 1H in DMSO showed pure compound contaminated by 2-MeTHF. The purity is 90.1% w/w) and was used in the next step without further purification.

This reaction proceeds very well. The yield and the quality of the product were high.

Step 2: Reduction of Ethyl Carbamate

To a suspension of LAH (31.0 g, 816 mmol, 2.5 eq) in dry THF (350 ml) at 15° C. (jacket temperature) was added a solution of ethyl cyclopentylcarbamate (57 g, 326 mmol, 1 eq) in dry THF (100 ml) keeping internal temperature below 20° C. over 1 b. Note: gas evolution was observed and controlled by rate addition.) The resulting slurry was slowly heated up to 45° C. (jacket temperature). (Note: The internal reaction temperature started to raise rapidly to solvent refluxing (internal temperature 69° C.) followed by foaming.) The jacket temperature was quickly cooled down to 0° C. to control the strong exothermic event. Within 30 minutes, the temperature cooled down and the jacket temperature was set to 55° C. The grey slurry was then stirred at 55° C. (jacket temperature) for 3 h. LC/MS showed no starting material left.

The resulting grey suspension was then cooled to 0° C., diluted with MTBE (225 mL, around 4.5 vol) To the grey slurry was added drop wise water (31 mL) over 2 h (Note: strong gas evolution and exothermic event), followed by 10% NaOH (46 mL). To the off-white suspension was added dropwise water (93 mL), the mixture was stirred 1 h at 20° C. then MgSO4 (104 g, 2 wt) was added. The resulting thick slurry was stirred for 1 h at 20° C., then filtered.

The cake was washed twice with MTBE (2×50 mL, 2×2 vol). The combined filtrates were cooled to 0° C. and concentrated HCl (32.6 ml, 392 mmol, 1.2 eq) was added. The resulting residue was stirred for 30 minutes at 0° C. and warmed to 20° C. and stirred overnight.

The mixture was then concentrated to 1 vol by distillation under reduced pressure (jacket temperature 60° C.), diluted with IPA (250 ml, 3 vol), concentrated to 1 vol under reduced pressure (jacket 60° C.) and finally diluted with IPA (100 mL, 2 vol), and concentrated to 1 vol under reduced pressure (Note: a crystalline solid is observed). To the residue were added DCM (50 mL, 1 vol) and MTBE (300 mL, around 5 vol). (Note: a biphasic system is observed.) Upon stirring, a hazy mixture is observed; the mixture was then cooled to 20° C. Within 10 minutes, crystallization occurs and the slurry was stirred for at least 1 h at 20° C., then filtered. The white crystalline solid was washed twice with MTBE (2×50 mL), then the solid was dried in a vacuum oven at 50° C. White crystalline N-methylcyclopentylamine hydrochloride (37.4 g, 85% yield) was obtained.

The invention claimed is:

1. A process for preparing a compound having the Formula A:

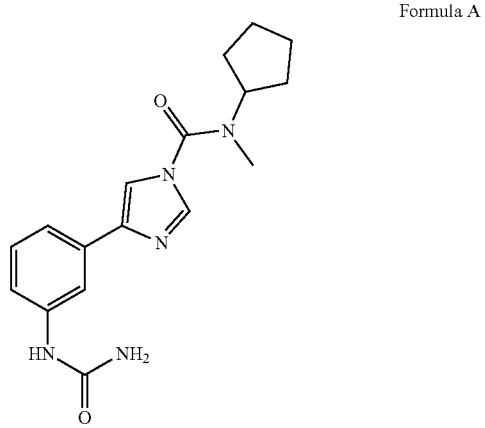 [SMILES: CN(C(=O)n1cnc(-c2cccc(NC(N)=O)c2)c1)C1CCCC1]

Formula A or a pharmaceutically acceptable salt or derivative thereof, the process comprising:

(a) oxidation of $R_6$—C(=O)—$CH_3$ to form a glyoxal intermediate $R_6$—C(=O)—CHO, wherein $R_6$ is $NH_2CONH$-phenyl, a nitrophenyl, aminophenyl, or amino-protected aminophenyl precursor thereof;

b) subjecting the glyoxal intermediate to treatment with ammonium hydroxide and an aldehyde, $CH_2O$, to provide an imidazolyl intermediate of Formula IIa':

Formula IIa' and (c) reacting the imidazolyl intermediate of Formula IIa' with a carbamoyl halide of the formula $NH_2C(=O)$Hal, wherein Hal represents Cl, F, I, or Br, thereby forming the compound having Formula A.

2. The process according to claim 1, wherein the oxidation of

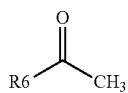

employs an inorganic acid.

3. The process according to claim 2, wherein the inorganic acid is HX, where X is a halogen atom.

4. The process according to claim 3, wherein the inorganic acid is HCl or HBr.

5. The process according to claim 1, wherein DMSO is used as a solvent and oxidising agent in the oxidation of

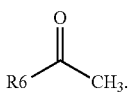

6. A process for preparing an imidazolyl intermediate of Formula IIa':

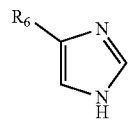

Formula IIa' or a pharmaceutically acceptable salt thereof, the process comprising the oxidation of

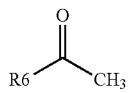

to form a glyoxal

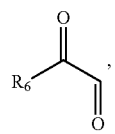

which is subjected to treatment with ammonium hydroxide and an aldehyde $CH_2O$ to provide the intermediate of Formula IIa', wherein $R_6$ is $NH_2CONH$-phenyl, a nitrophenyl, aminophenyl, or amino-protected aminophenyl precursor thereof.

7. The process according to claim 6, wherein the intermediate of Formula IIa' is extracted from the reaction mixture using a solvent comprising butanol.

8. A process for preparing the compound of Formula A as defined in claim 1, or a pharmaceutically acceptable salt or derivative thereof, the process comprising the reaction of an intermediate of Formula IIa' as defined in claim 1, with a carbamoyl halide of the formula: $R_1R_2NC(=O)Hal$, in a solvent consisting essentially of pyridine, wherein $R_6$ is $NH_2CONH$-phenyl, or a nitrophenyl, aminophenyl or an amino-protected aminophenyl precursor of this moiety which can be subjected to conversion to the $NH_2CONH$-phenyl group after urea formation, and $R_1$ is methyl and $R_2$ is cyclopentyl, and wherein Hal represents Cl, F, I or Br.

9. The process according to claim 8, further comprising treating the product mixture after urea formation with water.

10. The process according to claim 8, further comprising treating the product mixture after urea formation with a $C_{5-10}$ alkane or mixtures thereof.

11. The process according to claim 10, wherein the $C_{5-10}$ alkane comprises heptane.

12. The process according to claim 8, wherein the carbamoyl halide is a carbamoyl chloride.

* * * * *